United States Patent

Angehrn et al.

Patent Number: 5,935,950
Date of Patent: Aug. 10, 1999

[54] CEPHALOSPORIN PYRIDINIUM DERIVATIVES

[75] Inventors: Peter Angehrn, Böckten, Switzerland; Ingrid Heinze-Krauss, Schliengen, Germany; Malcolm Page, Basel; Urs Weiss, Pratteln, both of Switzerland

[73] Assignee: Hoffmann-La Roche Inc., Nutley, N.J.

[21] Appl. No.: 08/924,626

[22] Filed: Sep. 5, 1997

[30] Foreign Application Priority Data

Oct. 22, 1996 [EP] European Pat. Off. .............. 96116927

[51] Int. Cl.⁶ ...................... C07D 501/24; A61K 31/545
[52] U.S. Cl. ............................. 514/203; 540/225
[58] Field of Search ............... 540/225; 514/203

[56] References Cited

U.S. PATENT DOCUMENTS

| | | | |
|---|---|---|---|
| 5,275,816 | 1/1994 | Branch | 540/221 |
| 5,504,076 | 4/1996 | Branch | 540/225 |
| 5,523,400 | 6/1996 | Wei et al. | 540/221 |

FOREIGN PATENT DOCUMENTS 620225  10/1994  European Pat. Off. .

OTHER PUBLICATIONS

Heinze–Krauss, Ingrid, et al., *J. Med. Chem.*, 39:1864–1871 (1996).

*Primary Examiner*—Mark L. Berch
*Attorney, Agent, or Firm*—George W. Johnston; Patricia S. Rocha-Tramaloni; Alan P. Kass

[57] ABSTRACT

Compounds of formula I

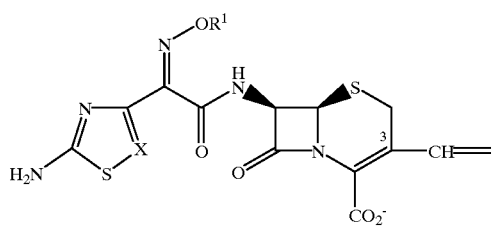

-continued

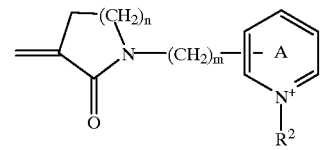

wherein $R^1$ is hydrogen, lower alkyl, cycloalkyl or acetyl;

x is CH or N;

n is 0, 1 or 2;

m is 0 or 1;

$R^2$ is hydrogen, lower alkyl, ω-hydroxy alkyl, benzyl or lower alkyl-heterocyclyl, the benzyl and the heterocyclyl group being unsubstituted or substituted with at least one of the groups amino, cyano, carboxy, halogen, hydroxy, lower alkyl, lower alkoxy or —$CONR_2$, where R is hydrogen or lower alkyl; or $R^2$ is —$CH_2CONR^4R^5$; wherein $R^4$, $R^5$ are each independently hydrogen, ω-hydroxy-alkyl, phenyl, benzyl, naphthyl or heterocyclyl, the phenyl, benzyl, naphthyl or heterocyclyl groups being unsubstituted or substituted with at least one of the groups optionally protected hydroxy, halogen, optionally substituted lower alkyl, optionally substituted lower alkoxy, ω-hydroxyalkyl or cyano; or $R^4$ and $R^5$ form together a group of formula

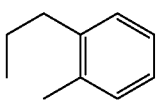

with the proviso that when pyridinium ring A is pyridinium-4-yl, m is 1; as well as readily hydrolysable esters thereof, pharmaceutically acceptable salts of said compounds and hydrates of the compounds of formula I and of their esters and salts. These compounds are useful as parenteral antibiotics.

164 Claims, No Drawings

CEPHALOSPORIN PYRIDINIUM DERIVATIVES

The present invention relates to compounds of formula I

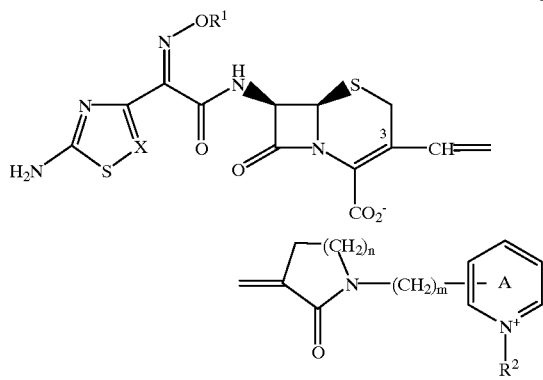

wherein
$R^1$ is hydrogen, lower alkyl, cycloalkyl or acetyl;
X is CH or N;
n is 0, or 2;
m is 0 or 1;
$R^2$ is hydrogen, lower alkyl, ω-hydroxy alkyl, benzyl or lower alkyl-heterocyclyl, the benzyl and the heterocyclyl groups being unsubstituted or substituted with at least one of the groups amino, cyano, carboxy, halogen, hydroxy, lower alkyl, lower alkoxy or —$CONR_2$, where R is hydrogen or lower alkyl; or $R^2$ is —$CH_2CONR^4R^5$; wherein
$R^4$, $R^5$ are each independently hydrogen, ω-hydroxy-alkyl, phenyl, benzyl, naphthyl or heterocyclyl, the phenyl, benzyl, naphthyl or heterocyclyl groups being unsubstituted or substituted with at least one of the groups optionally protected hydroxy, halogen, optionally substituted lower alkyl, optionally substituted lower alkoxy, ω-hydroxyalkyl or cyano;
or the groups $R^4$ and $R^5$ form together a group of formula

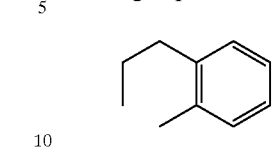

with the proviso that when pyridinium ring A is pyridinium-4-yl, m is 1;
as well as readily hydrolysable esters thereof, pharmaceutically acceptable salts of said compounds and hydrates of the compounds of formula I and of their esters and salts.

In above compounds of formula I the substituent in position 3 can be present in the E-form (formula Ia) or in the Z-form (formula Ib)

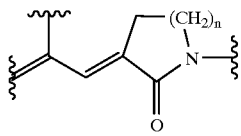

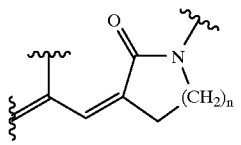

The pyridinium ring A is attached in 2, 3 or 4 position to the cephalosporin moiety as shown in the below formulae:

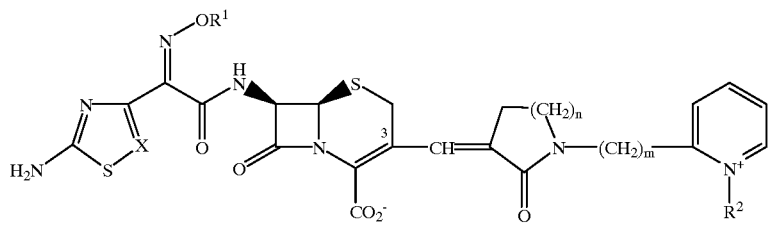

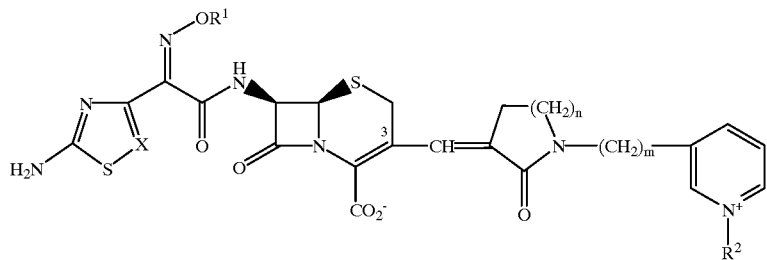

-continued

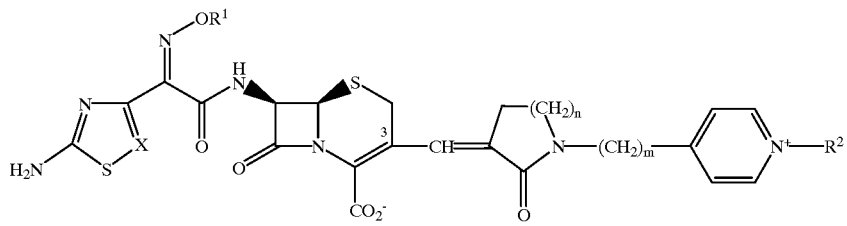

In a particular embodiment of the compounds of formula I, n is 1. Moreover $R^1$ is preferably hydrogen or cyclopentyl and $R^2$ is lower alkyl, ω-hydroxy alkyl, benzyl, the benzyl group being unsubstituted or substituted with at least one of the groups amino, cyano, carboxy, halogen, hydroxy, lower alkyl, lower alkoxy or —$CONR_2$, where R is hydrogen or lower alkyl, with the benzyl group being preferably substituted with one of the groups cyano, carboxy or hydroxy. Examples of especially preferred $R^2$ are methyl, ethyl, 2-hydroxyethyl, benzyl, 2-,3- or 4-hydroxybenzyl, 2-,3- or 4-cyanobenzyl, and 2-,3- or 4-carboxybenzyl.

In yet another particular embodiment $R^2$ is —$CH_2CONR^4R^5$. Especially preferred compounds of formula I wherein $R^2$ is —$CH_2CONR^4R^5$ are the compounds wherein $R^4$ is hydrogen and $R^5$ represents phenyl which is unsubstituted or substituted with at least one of the groups halogen, hydroxy, and lower alkoxy, such as, for example, hydroxyphenyl, 2-fluoro-4-hydroxy-phenyl, 3-fluoro-4-hydroxy-phenyl, 3-chloro-4-hydroxy-phenyl, 4-hydroxy-3-methoxy-phenyl.

The compounds of the formula I are preferably in the Z-form at the oximino group and E-form for the substituent in position 3 (formula Ia).

As used herein, the term "lower alkyl" refers to both straight and branched chain saturated hydrocarbon groups having 1 to 8 and preferably 1 to 4 carbon atoms, for example, methyl, ethyl, n-propyl, isopropyl, tertiary butyl and the like.

The term "lower alkoxy" refers to a straight or branched chain hydrocarbonoxy group wherein the alkyl portion is defined as above, for example, methoxy, ethoxy, propoxy, and the like.

By the term "cycloalkyl" is meant a 3-7 membered saturated carbocyclic moiety, for example, cyclopropyl, cyclobutyl, cyclopentyl, cyclohexyl, and the like.

By the term "optionally substituted lower alkyl, optionally substituted lower alkoxy" is understood both unsubstituted lower alkyl or lower alkoxy as defined above and lower alkyl or lower alkoxy substituted with at least one of halogen, especially fluorine, for example, fluoromethyl, trifluoromethyl, fluoroethyl, trifluoroethyl; or hydroxy, for example, 1-hydroxyethyl, 2-hydroxymethyl-propane-1,3-diol-2-yl; or amino or alkylamino, for example, 1-aminoethyl, 2-aminoethyl, 1-methylaminoethyl, and the like.

By the term "halogen" is meant fluorine or fluoro, chlorine or chloro, bromine or bromo, and iodine or iodo.

By the term "ω-hydroxy alkyl" is meant straight chain or branched alkyl groups with hydroxy-substituted terminal carbon atoms. Such groups are, for example, hydroxymethyl, 2-hydroxyethyl, 3-hydroxypropyl, propane-1,3-diol-2-yl, and the like.

By the term "lower alkylheterocyclyl" is meant a lower alkyl group as defined above substituted by a 4-, 5- or 6-membered heterocyclic ring, for example, azetidinyl, pyrrolidinyl, piperidinyl, pyridinyl, pyrimidinyl, pyrazidinyl, imidazolyl, triazolyl, tetrazolyl, thiadiazolyl, isoxazolyl, oxazolyly, and the like.

Examples of "benzyl and heterocyclyl substituted with at least one of the groups of amino, cyano, carboxy, halogen, hydroxy, lower alkyl, lower alkoxy or —$CONR_2$, R being hydrogen or lower alkyl" are 2-, 3- or 4-cyanobenzyl, 2-, 3- or 4-hydroxybenzyl, 2,4-dihydroxybenzyl, 3,4-dihydroxybenzyl, 2-, 3- or 4-carboxybenzyl.

Examples of "phenyl, benzyl, naphthyl or heterocyclyl unsubstituted or substituted with at least one of the groups optionally protected hydroxy, halogen, optionally substituted lower alkyl, optionally substituted lower alkoxy, ω-hydroxyalkyl or cyano" are 2-, 3- or 4-fluorophenyl, 2-, 3- or 4-chlorophenyl, 2-, 3- or 4-hydroxyphenyl, 2-, 3- or 4-methoxyphenyl, 2-fluoro-4-hydroxyphenyl, 3-fluoro-4-hydroxyphenyl, 2-methoxy-4-hydroxyphenyl, 3-methoxy-4-hydroxyphenyl, 3-chloro-4-hydroxyphenyl, 3-hydroxybenzyl, and the like.

The term "optionally protected hydroxy" refers to hydroxy or hydroxy protected with, for example, t-butyloxycarbonyl, trimethylsilyl, t-butyl-dimethylsilyl, tetrahydropyranyl, trifluoroacetyl, or refers to an ester group, or example, phosphate, sulfonate and the like.

As used herein "pharmaceutically acceptable salts" useful in this invention include salts derived from metals, the ammonium salt, quaternary ammonium salts derived from organic bases and amino acid salts. Examples of preferred metal salts are those derived from the alkali metals, for example, lithium ($Li^+$), sodium ($Na^+$) and potassium ($K^+$). Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like. Those salts derived from amines include salts with N-ethylpiperidine, procaine, dibenzylamine, N,N'-dibenzylethylenediamine, alkylamines or dialkylamines as well as salts with amino acids such as, for example, salts with arginine or lysine. Further especially preferred salts are hydrochlorides, sulfates, phosphates, lactates, mesylates or the inner salt.

As readily hydrolysable esters of the compounds of formula I there are to be understood compounds of formula I, the carboxy group(s) of which (for example, the 2-carboxy group) is/are present in the form of readily hydrolysable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)carbonyl]oxy] ethyl ester; 1-(acetyloxy) ethyl ester; (5-methyl-2-oxo-1,3-dioxol-4-yl) methyl ester; 1-[[(cyclohexyloxy)carbonyl]oxy] ethyl ester; and 3,3-dimethyl-2- oxobutyl ester. It will be appreciated by those of ordinary skill in the art that the readily hydrolysable esters of the compounds of the present invention can be formed at a free carboxy group of the compound, for example, at the carboxy group in position 1 or any other carboxy group.

Preferred compounds of formula I include:
(6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

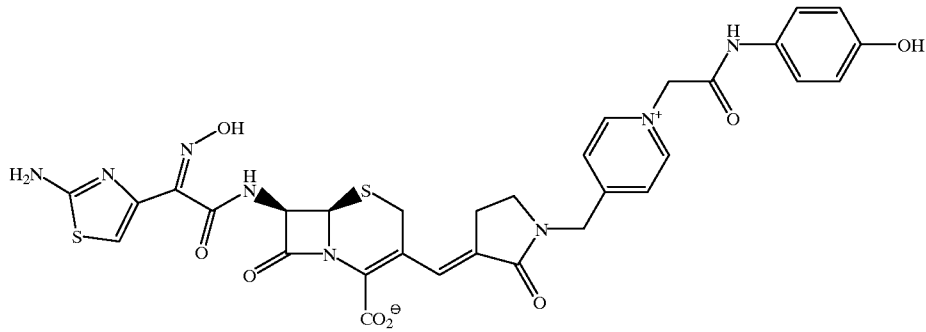

(6R,7R)-7-[(Z)-2-(5-Amino-[1,2,4]thiadiazol-3-yl)-2-hydroxyiminoacetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

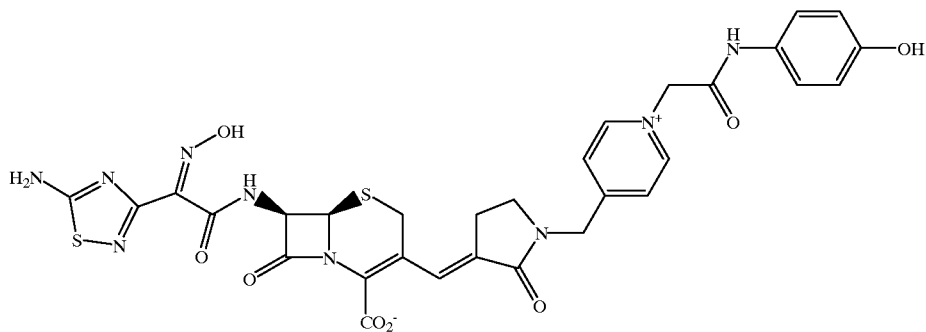

(6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia- 1-aza-bicyclo[4.2.0]oct-2-ene-2-carboxylate

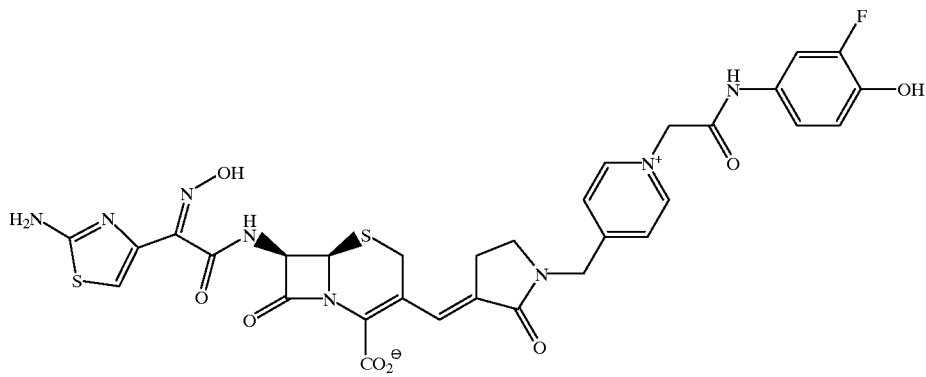

(6R,7R)-7-[(Z)-2-(5-Amino-[1,2,4]thiadiazol-3-yl)-2-hydroxyiminoacetylamino]-3-[(E )-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

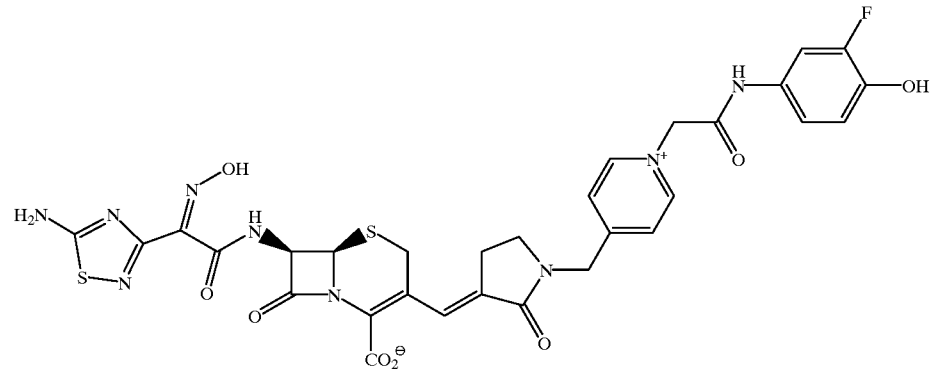

(6R,7R)-7-[(Z)-2-(2-Amino-thiazol-4-yl)-2-hydroxyiminoacetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

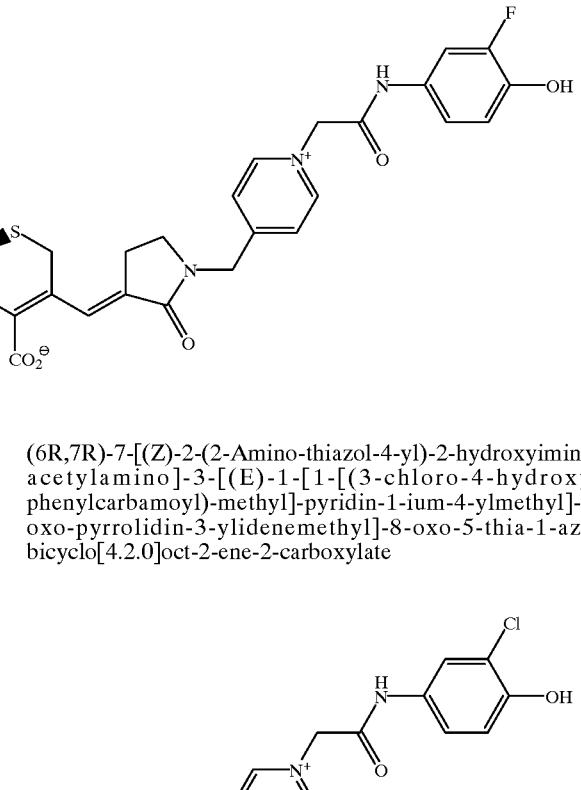

(6R,7R)-7-[(Z)-2-(2-Amino-thiazol-4-yl)-2-hydroxyiminoacetylamino]-3-[(E)- 1-[1-[(4-hydroxy-3-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate

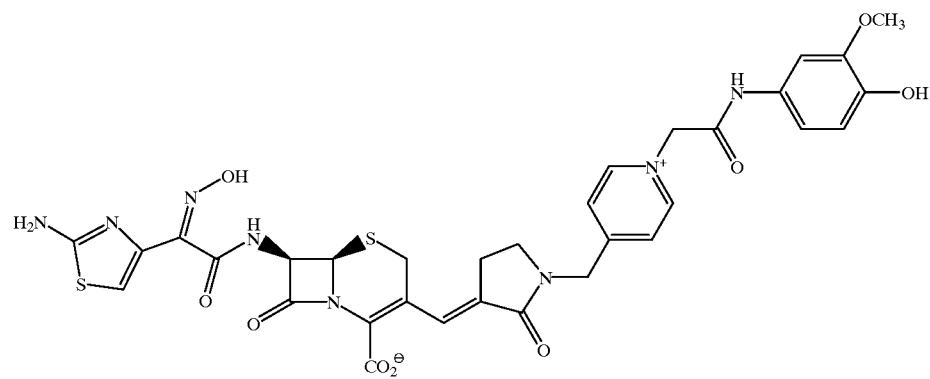

(6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin- 1-ium-3-ylmethyl]-2-oxo-pyrrolidin-3-ylidenemethyl]-8-oxo-5-thia-1-aza-bicyclo[4.2.0]oct-2-ene-2-carboxylate hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]-oct-2-ene-2-carboxylate D: (6R,7R)-7-[(Z)-2-(5-Amino-[1,2,4]thiadiazol-3-yl)-2-hydroxyimino-acetylamino]-3-[(E)-1-[1-[(3-fluoro-4-

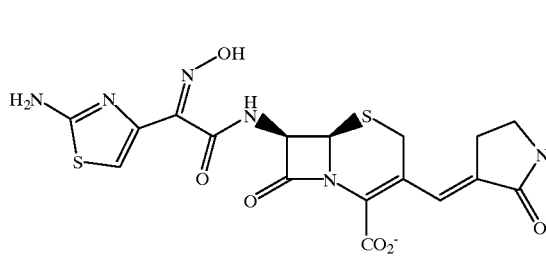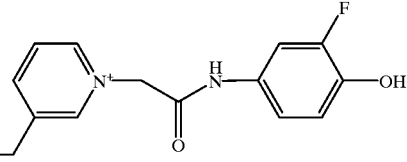

The invention also relates to pharmaceutical compositions and methods of use of the above.

The compounds of formula I as well as their salts and readily hydrolysable esters can be hydrated. The hydration can be effected in the course of making the compounds or can occur gradually as a result of hygroscopic properties of an initially anhydrous product.

The compounds of the present invention are useful as antibiotics having potent and broad antibacterial activity, especially against methicillin-resistant staphylococci (MRSA), enterococci and pneumococci infections in mammals, both human and non-human.

The products in accordance with the invention can be used as medicaments, for example, in the form of pharmaceutical preparations for parenteral administration, and for this purpose are preferably made into preparations as lyophilisates or dry powders for dilution with customary agents, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds of the present invention were tested.

In vitro activity was determined by minimum inhibitory concentration in a microorganism spectum by the agar dilution method in Mueller Hinton agar.

The following compounds were tested:

A: (6R,7R)-7-[(Z)-2-(2-Amino-thiazol-4-yl)-2-hydroxyimino-acetylamino]-3-[(E)- 1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate B: (6R,7R)-7-[(Z)-2-(5-Amino-[1,2 ,4]thiadiazol-3-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]-oct-2-ene-2-carboxylate C: (6R,7R)-7-[(Z)-2-(2-Amino-thiazol-4-yl)-2-hydroxyimino-acetylamino]-3-[(E)-1-[1-[(3-fluoro-4- hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate E: (6R,7R)-7-[(Z)-2-(2-Amino-thiazol-4-yl)-2-hydroxyimino-acetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia- 1-aza-bicyclo[4.2.0]-oct-2-ene-2-carboxylate F: (6R,7R)-7-[(Z)-2-(2-Amino-thiazol-4-yl)-2-hydroxyimino-acetylamino]-3-[(E)-1-[1-[(4-hydroxy-3-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]-oct-2-ene-2-carboxylate G: (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]-oct-2-ene-2-carboxylate The antibacterial Spectrum appears below:

| MIC : Minimum Inhibiting Concentration Values In vitro activity against sensitive and resistant S. aureus | | | | | | | |
|---|---|---|---|---|---|---|---|
| | A | B | C | D | E | F | G |
| MIC S. aureus 6538 (MSSA)* | 0.5 | 0.5 | 1 | 1 | 0.5 | 1 | 0.5 |
| MIC S. aureus 42080 (MRSA)* | 4 | 4 | 4 | 4 | 4 | 8 | 4 |
| MIC MRSA (n=17)** | 8 | 4 | 4 | 4 | 8 | 8 | 8 |

MIC [µg/ml]; agar dilution method on Mueller-Hinton agar.
*inoculum $10^4$ CFU/spot
**inoculum $10^5$ CFU/spot The compounds of the formula I in accordance with the invention as well as their pharmaceutical acceptable salts, hydrates, or readily hydrolyzable esters can be made in accordance with the invention by (a) treating a compound having the formula II

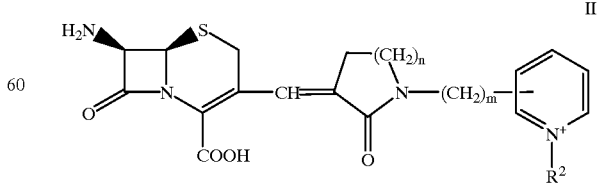

in which $R^2$, m and n are defined above, or an ester or salt thereof, with a carboxylic acid of formula III

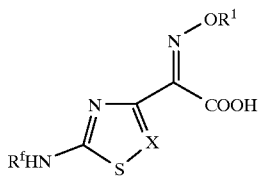

in which $R^f$ is hydrogen or an amino protecting group, $R^1$ and X are defined above, or a reactive functional derivative thereof, or (b) cleaving off the amino, hydroxy and/or carboxy protecting group in a compound having the formula IV

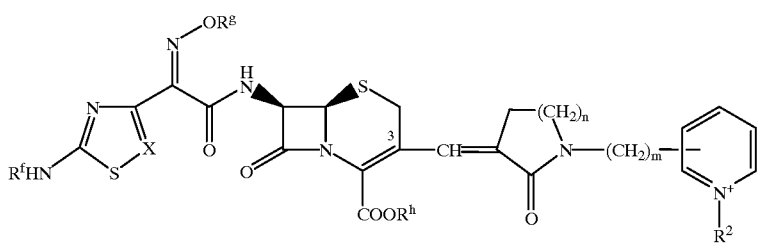

in which $R^2$, m and n are defined above, $R^f$ is hydrogen or an amino protecting group, $R^g$ is hydrogen or a hydroxy protecting group, $R^h$ is hydrogen or a carboxy protecting group, provided that at least one of $R^f$, $R^g$ and $R^h$ is a corresponding protecting group or a salt thereof, or (c) alkylation of a compound of formula

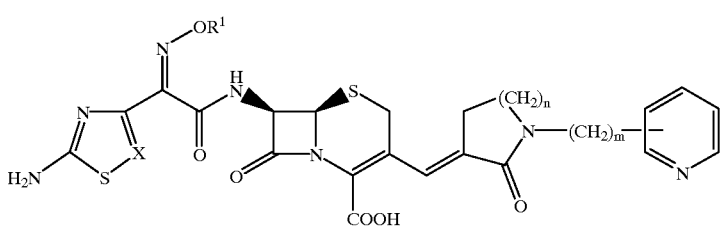

wherein $R^1$, X, m and n are as defined above, with a alkylating agent such a methyliodide, dimethylsulfate, trimethyloxonium tetrafluoroborate, bromo-, iodoacetamide or Br—$CH_2$—$CONR^4R^5$, wherein $R^4$ and $R^5$ are as defined above, or (d) making a readily hydrolysable ester of a compound of formula I subjecting a carboxylic acid of formula I to a corresponding esterification, or (e) making salts or hydrates of a compound of formula I or hydrates of said salts converting a compound of formula I into a salt or hydrate or into a hydrate of said salts.

The reaction of compounds of formula II and III or a reactive derivative of of formula III according to embodiment (a) can be carried out in a manner known to those skilled in the art. The carboxy group in compounds of formula II can be protected; for example, by esterification to form a readily cleavable ester such as a silyl ester (e.g. the trimethylsilyl ester) p-methoxybenzyl or benzhydryl ester.

The amino group present in the acylating agent of formula III can be protected. Possible protecting groups $R^f$ are, for example, protecting groups which are cleavable by acid hydrolysis (e.g. the tert.butoxycarbonyl or trityl groups), by basic hydrolysis (e.g. the trifluoroacetyl group) or by hydrazinolysis (e.g. the phthalimido group). Preferred protecting groups are the t-butyloxy-carbonyl, phenylacetyl, the chloroacetyl, bromoacetyl and iodoacetyl groups, especially the chloroacetyl group. These last-mentioned protecting groups can be cleaved off by treatment with thiourea. The 7-amino group in compounds II can be protected, for example, by a silyl protecting group such as the trimethylsilyl group.

In reacting a 7-amino compound of formula II with a carboxylic acid of formula III or a reactive functional derivative thereof, for example, a free carboxylic acid can be reacted with an aforementioned ester of a compound of formula II in the presence of a carbodiimide such as dicyclohexylcarbodiimide in an inert solvent such as ethyl acetate, acetonitrile, dioxane, chloroform, methylene chloride, benzene or dimethylformamide, and subsequently the ester group can be cleaved off.

According to another embodiment, a salt of an acid of formula II (e.g. a trialkylammonium salt such as the triethylammonium salt) is reacted with a reactive functional derivative of a carboxylic acid of formula III in an inert solvent (e.g. tetrahydrofurane, dichhloromethane, dimethylformamide and dimethylsulfoxide).

According to a further embodiment, preferred acylation, where the amino group present in the acylating agent of formula III need not be protected, involves the use of a 2-benzothiazolyl thioester, a 1-hydroxybenzotriazole ester or a mixed anhydride of thiophosphoric acid of the carboxylic acid. For instance, the 2-benzthiazolyl thioester may be reacted with the compound II in an inert organic solvent such as a chlorinated hydrocarbon e.g. methylene chloride, or in dimethylformamide, dimethyl-sulfoxide, acetone, ethyl acetate or in a mixture of such solvents with water. The 1-hydroxybenzotriazole ester can be employed by reacting the carboxylic acid with 1-hydroxybenzotriazole and a carbodiimide, especially N,N'-dicyclohexylcarbodiimide or N,N'-diisopropylcarbodiimide in an inert organic solvent, preferably methylene chloride, dimethylformamide, dimethyl-sulfoxide, tetrahydrofuran, acetonitrile or ethyl acetate.

The reaction of a 7-amino compound of formula II with the carboxylic acid of formula III or a reactive derivative thereof can conveniently be carried out at a temperature between about −40° C. and +60° C., e.g. at room temperature.

Embodiment (b) of the process of the present invention involves deprotection (removal) of protected amino, hydroxy or carboxylic groups present in a compound of formula IV and can be carried and as follows:

Removal of amino protecting groups

Possible amino-protecting groups are those employed in peptide chemistry, such as an alkoxycarbonyl group, e.g., t-butoxycarbonyl, allyloxy carbonyl etc., a substituted alkoxycarbonyl group, e.g., trichloroethoxycarbonyl etc., an optionally substituted aralkyloxycarbonyl group, e.g., p-nitrobenzyloxycarbonyl or benzyloxycarbonyl, an aralkyl group such as trityl or benzhydryl or a halogen-alkanoyl group such as chloroacetyl, bromoacetyl, iodoacetyl or trifluoroacetyl.

Preferred protecting groups are t-butoxycarbonyl (t-BOC) and trityl.

The amino protecting groups may be cleaved off by acid hydrolysis (e.g. the t-butoxycarbonyl or trityl group), e.g. aqueous formic acid, trifluoroacetic acid or by basic hydrolysis (e.g. the trifluoroacetyl group). The chloroacetyl, bromoacetyl and iodoacetyl groups are cleaved off by treatment with thiourea.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about −30° C. to +40° C.). Protecting groups which are cleavable under basic conditions are generally hydrolyzed with dilute aqueous caustic alkali at 0° C. to 30° C. The chloroacetyl, bromoacetyl and iodoacetyl protecting groups can be cleaved off using thiourea in acidic, neutral or alkaline medium at about 0° C.–30° C.

Removal of hydroxy protecting groups

Possible hydroxy protecting groups are such as are commonly known in the art, e.g.

for protection of hydroxyimino groups ($R^1$=hydrogen in compounds of formula I), usually trityl, lower alkanoyl, preferably acetyl, tetrahydropyranyl protecting groups are employed.

These protecting groups are e.g. removed as follows:

| | |
|---|---|
| -trityl | in acidic solvents like 90% formic acid at about 0 to 50° C. or triethylsilane in trifluoroacetic acid at about −20 to 25° C.; in organic solutions of hydrochloric acid at about −50 to 25° C.; |
| -acetyl | with weak inorganic bases like sodium bicarbonate in methanol or ethanol/water at about 0 to 50° C.; |
| -tetrahydropyranyl | with weak organic acids like p-toluenesulfonic acid in an alcohol, e.g. ethanol, at about 0° C. to the boiling point of the mixture. |

Removal of protecting groups at the carboxy function

As carboxyl protecting groups one may utilize an ester form which can be easily converted into a free carboxyl group under mild conditions, for example, benzhydryl, t-butyl, p-nitrobenzyl, p-methoxybenzyl, allyl, etc.

These protecting groups may be removed as follows:

| | |
|---|---|
| benzhydryl | trifluoroacetic acid with anisol, phenol, cresol or triethylsilane at about −40° C. to room temperature; hydrogen with Pd/C in an alcohol such as ethanol or in tetrahydrofuran; $BF_3$-etherate in acetic acid at about 0 to 50° C.; |
| t-butyl | formic acid or trifluoroacetic acid with or without anisol, phenol, cresol or triethylsilane and a solvent such as dichloromethane at about −10° C. to room temperature; |
| p-nitrobenzyl | sodium sulfide in acetone/water at about 0 to room temperature; or hydrogen with Pd/C in an alcohol such as ethanol or in tetrahydrofuran; |
| p-methoxybenzyl | formic acid at about 0 to 50° C.; or trifluoroacetic acid and anisol, phenol or triethylsilane at about −40° C. to room temperature; |
| allyl | palladium(O) catalyzed transalkylation reaction in the presence of sodium or potassium salt of 2-ethyl hexanoic acid, see for example J. Org. Chem. 1982, 47, 587. |

In order to make a readily hydrolysable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0–40° C.

Making the salts and hydrates of the compounds of formula I or the hydrates of said salts in accordance with embodiment (d) of the process provided by the present invention can be carried out in a manner known to those skilled in the art; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt or acid. The temperature at which the salt formation is carried out is not critical. The salt formation is generally carried out at room temperature, but it can be carried out at a temperature slightly above or below room temperature, for example in the range of 0° C. to +50° C.

Making the hydrates usually takes place automatically in the course of making the compound or as a result of the hygroscopic properties of an initially anhydrous product. For the controlled making of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction schemes 1 and 2 below.

Scheme 1
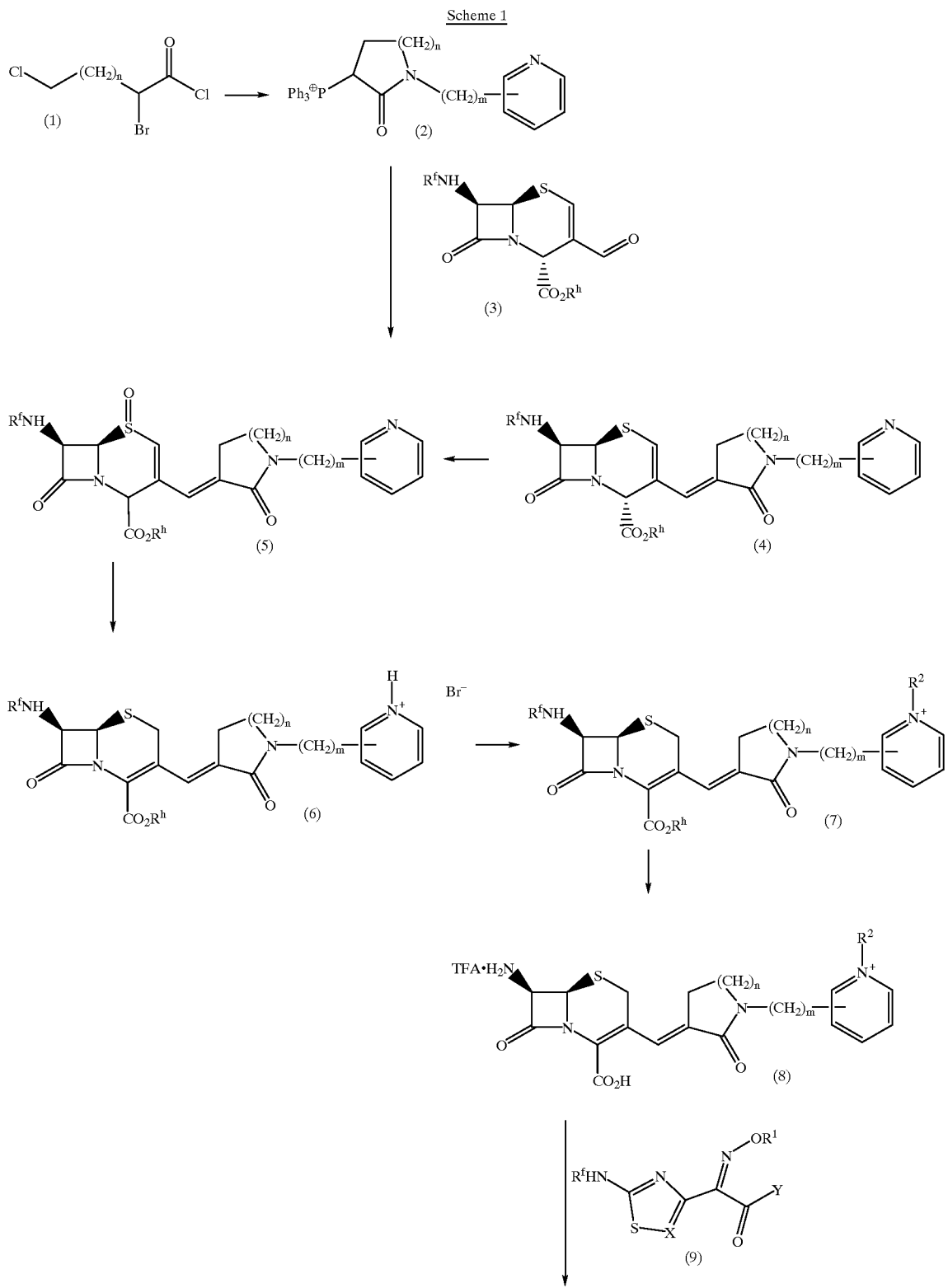

-continued

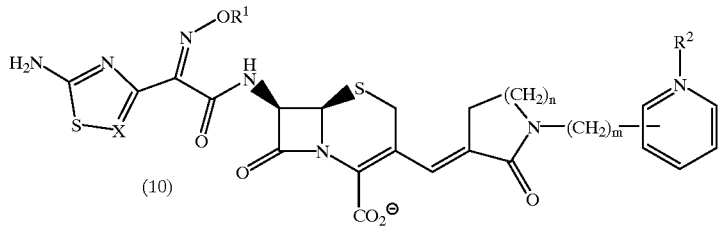
(10)

wherein n is 1 or 2, Y is OH, halogen or an activating group, for example, the 2-benzothiazolylthioester, the 1-hydroxybenzotriazole or a mixed anhydride of thiophosphonic acid and the remaining symbols are as defined above.

amino-pyridine (for m=0) or a picolylamine (for m =1) to form the corresponding bromolactam which is subsequently treated with triphenylphosphine in solvents like tetrahydrofuran (THF), dimethylformamide (DMF) or the like.

Scheme 2

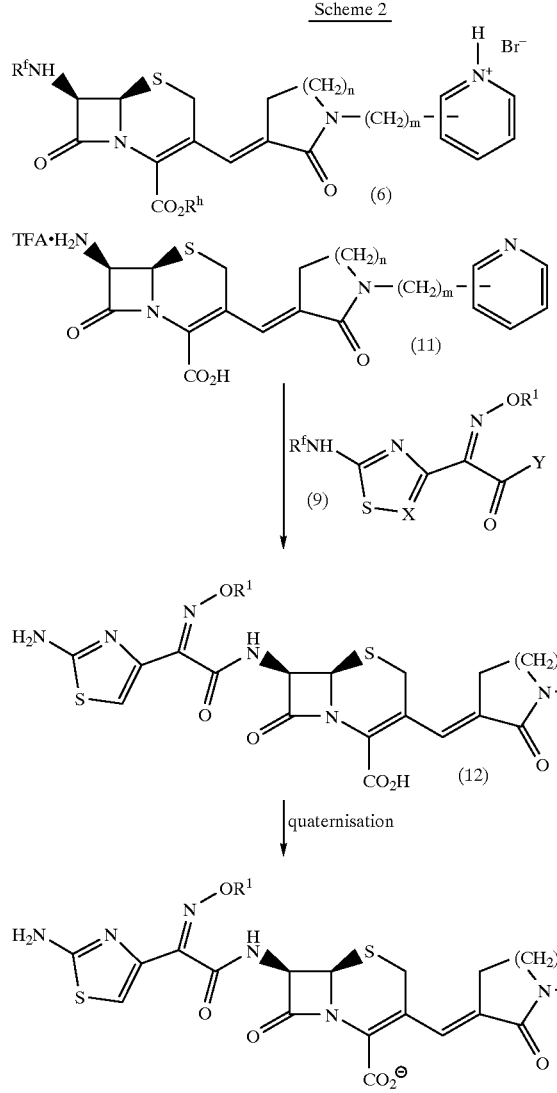

(1)→(2)

The known α-bromo-ω-chloro acide chloride (1) is converted into a Wittig reagent (2) by firstly reacting it with a (2)→(4)

The reaction of known 2-cephem aldehyde (3) where $R^h$ is a carboxy protecting group as defined above, e.g. benzhydryl ester, and $R^f$ is an amino protecting group as defined above, e.g. tert. butyloxycarbonyl, with a Wittig reagent, exemplified by structure (2), yields the cephalosporin moiety (4). The reaction is carried out in the presence of a base which is either an inorganic base (sodium or potassium hydroxide, sodium or potassium carbonate etc.), an organic base (tertiary amines, potassium tert.butoxide), an organolithium such as butyl lithium or phenyllithium or an epoxide such as 1,2-butyleneoxide. The reaction in presence of an epoxide is preferred. The preferred solvents, in the case of inorganic base being used, are water and water-miscible solvent (acetone, tetrahydrofuran, or alcohols etc.); in the case of organic base being used, an inert solvent such as methylene chloride, dicloroethane, chloroform, benzene, tetrahydrofuran; in the case of organolithium being used, benzene or tetrahydrofuran; and in the case an epoxide being used, the epoxide itself (e.g. 1,2-butyleneoxide or in mixture with e.g. dichloroethane). The temperature for the reaction ranges from −20° C. to 80° C. The preferred conditions are exemplified in the examples.

In the normal Wittig reaction according to scheme 1, the E isomer is the predominant product. Invariably, less than 10% Z-isomer is formed, the amount depending on the reagents and conditions.

(4)→(5)

Compound (4) is converted to the sulfoxide (5) with an oxidizing agent, for example, hydrogen peroxide or a peracid, preferably 3-chloroperbenzoic acid. The temperature ranges from −20° C. to room temperature and any suitable solvent, preferably chlorinated hydrocarbon or benzene can be used.

(5)→(6)

The de-oxygenation of the sulfoxide (5) is carried out in the presence of phosphorus tribromide in dimethylformamide or in the mixed solvent of dimethylformamide and N-methylacetamide. The reaction temperature for the reaction is from about −78° C. to about 0° C.

(6)→(7) and (12)→(10) (see Scheme 2)

The N-alkylation of (6) respectively (12) is preferably performed in an inert solvent, for example, dimethylformamide (DMF) using an appropriate halogen-derivative.

(7)→(8)

The protecting groups $R^f$ and $R^h$ are removed and the reaction conditions used are depending on the nature of the protecting groups. In the case of $R^f$ being tert-butoxycarbonyl and $R^h$ being benzhydryl, trifluoroacetic acid and anisole or triethylsilane is employed, at temperature of about −20° C. to about room temperature (about 22° C.).

(8)→(10) and (11)→(12)

The acylation of compound (8), respectively (11) can be carried out with an organic acid (9) which is activated with known reagents Y, preferably thionyl chloride, oxalyl chloride, dicyclohexylcarbodiimide, bis-[benzthiazolyl-(2)] disulfide, N-hydroxy-benzotriazole, a 2-halo N-methyl-pyridinium salt or a mixed anhydride of thiophosphoric acid e.g. of diethylthiophosphoric acid. The reaction is carried out with or without the base (inorganic or organic bases) depending on the method of activation and a wide range of solvents, from water and water-miscible solvent to inert solvents such as chloroform, dichloroethane, dimethylformamide (DMF) or dimethylsulfoxide (DMSO) can be used. The substituents in the $R^1$ group, if necessary, can be further deprotected with a reaction condition suitable for the removal of the protecting group.

(12)→(10)

The quaternisation of the pyridyl ring may be performed subsequent to the isomerisation steps (4)→(6) as described above or subsequent to the acylation step (11)→(12) (scheme 2). However, quaternisation after acylation requires intermediate protection of the other sensitive groups in compound (12).

EXAMPLE 1 preparation (1) ⟶ (2), scheme 1

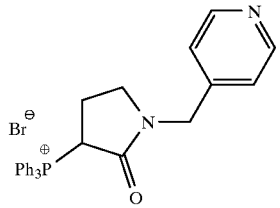

1.1. (RS)-(2-Oxo-1-pyridin-4ylmethyl-pyrrolidin-3-yl)-triphenyl-phosphonium bromide A stirred solution of 4-picolylamine (6.7 ml, 0.067 mol) and triethylamine (9.3 ml, 0.067 mol) in 400 ml dichloromethane was treated within 30 min at −55° C. with a solution of 2-bromo-4-chloro-butanoyl chloride (14.67 g, 0.067 mol) in 100 ml dichloromethane. The reaction mixture was stirred at −50° C. to −10° C. for 3.5 h and then poured on 200 ml ice/water. The phases were separated, the organic phase was washed once with 200 ml ice/water before it was concentrated to a volume of about 400 ml.

To the organic phase was added 1.2 g Dowex 2x10 and the vigorously stirred mixture was treated within 20 min. at 0° C. with 170 ml 50% aqueous sodium hydroxide solution. The mixture was allowed to warm up to room temperature and was stirred for 18 h. The phases were separated, the aqueous phase was extracted once with 170 ml dichloromethane. The combined organic phases were washed twice with 200 ml ice/water, once with brine and were dried over magnesium sulfate. After filtration they were reduced to a volume of about 30 ml and purified by column chromatography (50 g SiO$_2$, ethyl acetate). The fractions containing pure material were combined and reduced to a volume of 300 ml.

Triphenylphosphine (17.5 g, 0.067 mol) and 50 ml DMF were added to the solution before dichloromethane was removed in vacuo. The residual solution was heated at 80° C. for 4 h. The residue was dissolved in dichloromethane and water, the phases were separated and the aqueous phase was extracted thrice with dichloromethane. The combined organic phases were washed once with water, dried over magnesium sulfate and after filtration concentrated to a volume of 200 ml. This solution was added dropwise with stirring to 1000 ml diethylether upon which the product separated. It was collected by filtration, washed with diethylether and dried in vacuo, yielding 10.3 g (30%) colorless crystals.

IR(KBr) 1689, 1641 cm$^{-1}$; MS(ISP) 437.4 (M+H)$^+$.

According to the procedure set forth in the preceding example, the following compounds were prepared:

1.2. (RS)-(2-Oxo-1-pyridin-3-ylmethyl-pyrrolidin-3-yl)-triphenyl-phosphonium bromide IR (KBr) 1686 cm$^{-1}$, MS (ISP) 438.6 (M−H)$^+$ 1.3. (RS)-(2-Oxo-1-pyridin-2-ylmethyl-pyrrolidin-3-yl)-triphenyl-phosphonium bromide IR (KBr) 1687 cm$^{-1}$, MS (ISP) 437.5 M$^+$

EXAMPLE 2 preparation (2) ⟶ (4), scheme 1

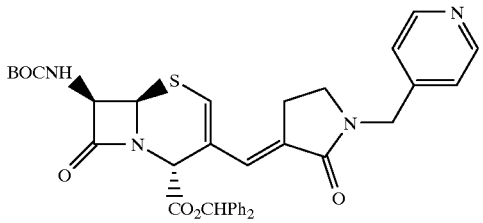

2.1. (E)-(2R,6R,7R)-7-tert-Butoxycarbonylamino-8-oxo-3-(2-oxo-1-pyridin-4-ylmethyl-pyrrolidin-3-ylidenemethyl)-5-thia-1-aza-bicyclo[4.2.0]oct-3-ene-2-carboxylic acid benzhydryl ester A suspension of (RS)-(2-oxo-1-pyridin-4-ylmethyl-pyrrolidin-3-yl)-triphenylphosphonium bromide (62.0 g, 0.12 mol) and (2R,6R,7R)-tert-butoxycarbonylamino-3-formyl-8-oxo-5-thia-1-azabicyclo[4.2.0]oct-3-ene-2-carboxylic acid benzhydryl ester (65.3 g, 0.13 mol) in a mixture of 300 ml butylenoxide and 300 ml dichloroethane were refluxed for 3.5 h. The solvent was removed in vacuo and the residue was purified by column chromatography (1000 g $SiO_2$, ethyl acetate) yielding 70.0 g (89%) of the product as a orange-red foam.

IR(KBr) 1780, 1743, 1714 $cm^{-1}$; MS(ISP) 653.4 $(M+H)^+$.

According to the procedure set forth in the preceding example, the following additional compounds were prepared:

2.2. (E)-(2R,6R,7R)-7-tert-Butoxycarbonylamino-8-oxo-3-(2-oxo-1-pyridin-3-ylmethyl-pyrrolidin-3-ylidenemethyl)-5-thia-1-aza-bicyclo[4.2.0]oct-3-ene-2-carboxylic acid benzhydryl ester IR (KBr) 1781, 1743, 1716 $cm^{-1}$, MS (ISP) 653.2 $(M+H)^+$ 2.3. (E)-(2R,6R,7R)-7-tert-Butoxycarbonylamino-8-oxo-3-(2-oxo-1-pyridin-2-ylmethyl-pyrrolidin-3-ylidenemethyl)-5-thia- 1-aza-bicyclo[4.2.0]oct-3-ene-2-carboxylic acid benzhydryl ester IR (KBr) 1781, 1744 $cm^{-1}$, MS (ISP) 653.4 $(M+H)^+$

EXAMPLE 3 preparation (4) ⟶ (5), scheme 1

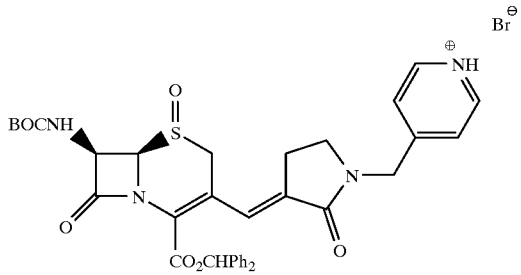

3.1. Mixture of (E)-(5R,6R,7R)- and -(5S,6R,7R)-7-tertbutoxycarbonyamino-5,8-dioxo3-(2-oxo-1-pyridin4-ylmethyl-pyrrolidin-3-ylidenemethyl)-5-thia-1-aza-bicyclo[4.2.0]oct-2-ene-2-carboxylate acid benzhydryl ester A solution of (E)-(2R,6R,7R)-7-tert-butoxycarbonylamino-8-oxo-3-(2-oxo-1-pyridin-4-ylmethyl-pyrrolidin-3-ylidenemethyl)-5-thia-1-aza-bicyclo[4.2.0]oct-3-ene-2-carboxylic acid benzhydryl ester (70.0 g, 0.11 mol) in 700 ml dichloromethane was cooled to −10° C. To this was added dropwise a solution of m-chloroperbenzoic acid (70%, 29.0 g, 0.12 mol) in 400 ml dichloromethane. After 4.5 h at −10° C., 400 ml aqueous sodium thiosulfate solution (10%) was added and the mixture was stirred for 15 min. The phases were separated and the organic phase was washed with each 400 ml of aqueous solutions of sodium thiosulfate (10%), sodium bicarbonate (10%) and finally brine. The solution was dried over magnesium sulfate, concentrated after filtration and purified by column chromatography (1000 g $SiO_2$, gradient of ethyl acetate and methanol). The fractions containing the pure product were collected, concentrated and added dropwise to hexane. The product separated yielding 45.0 g (61%) beige crystals.

IR(KBr) 1794, 1720 $cm^{-1}$; MS(ISP) 669.4 $(M+H)^+$.

According to the procedure set forth in the preceding example, the following additional compounds were prepared:

3.2. Mixture of (E)-(5R,6R,7R)- and -(5S,6R,7R)-7-tert-butoxycarbonylamino-5,8-dioxo-3-(2-oxo-1-pyridin-3-ylmethyl-pyrrolidin-3-ylidenemethyl)-4-thia-1-aza-bicyclo[4.2.0]oct-2-ene-2-carboxylic acid benzhydryl ester IR (KBr) 1795, 1721 $cm^{-1}$, MS (ISP) 669.3 $(M+H)^+$ 3.4. Mixture of (E)-(5R,6R,7R)- and -(5S,6R,7R)-7-tert-butoxycarbonylamino-5,8-dioxo-3-(2-oxo-1-pyridin-2-ylmethyl-pyrrolidin-3-ylidenemethyl)-5-thia-1-aza-bicyclo[4.2.0]oct-2-ene-2-carboxylic acid benzhydryl ester IR (KBr) 1795, 1721 $cm^{-1}$, MS (ISP) 669.3 $(M+H)^+$

EXAMPLE 4 preparation (5) ⟶ (6), scheme 1

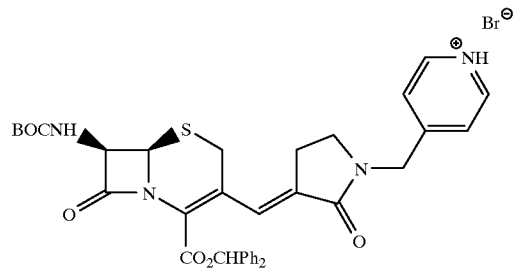

4.1. (E)-(6R,7R)-7-tert-Butoxycarbonylamino-8oxo-(2oxo1-pyridin-4-ylmethyl-pyrrolidin-3-ylidenemethyl)-5-thia-1-aza-bicyclo[4.2.0]oct-2-ene-2-carboxylic acid benzhydryl ester hydrobromide A solution of a mixture of (E)-(5R,6R,7R)- and -(5S,6R,7R)-7-tert-butoxycarbonylamino-5,8-dioxo-3-(2-oxo-1-pyridin-4-ylmethyl-pyrrolidin-3-ylidenemethyl)-5-thia-1-aza-bicyclo[4.2.0]oct-2-ene-2-carboxylate acid benzhydryl ester (45 g, 0.067 mol) in 600 ml dichloromethane, 60 ml DMF and 40 ml N-methylacetamide was treated at −78° C. with phosphorous tribromide (26 ml, 0.269 mol). After 3.5 h the mixture was allowed to warm up to −5° C., quenched with 500 ml water and the pH was adjusted to 3.5 using 4N sodium hydroxide solution. The phases were separated, the aqueous phase was extracted once with 600 ml dichloromethane, the combined organic phases were washed once with 500 ml water and dried over magnesium sulfate. After concentration, the solution was added dropwise into 1500 ml hexane, upon which the product separated, yielding 40.1 g (92%) yellowish crystals.

IR(KBr) 1784, 1719 $cm^{-1}$; MS(ISP) 653.5 $(M+H)^+$.

According to the procedure set forth in the preceding example, the following additional compounds were prepared:

4.2. (E)-(6R,7R)-7-tert-Butoxycarbonylamino-8-oxo-3-(2-oxo-1-pyridin-3-ylmethyl-pyrrolidin-3-ylidenemethyl)-5-thia-1-aza-bicyclo[4.2.0]oct-2-ene-2-carboxylic acid benzhydryl ester IR (KBr) 1784, 1718 cm$^{-1}$, MS (ISP) 675.3 (M+Na)$^+$
4.3. (E)-(6R,7R)-7-tert-Butoxycarbonylamino-8-oxo-3-(2-oxo-1-pyridin-2-ylmethyl-pyrrolidin-3-ylidenemethyl)-5-thia-1-aza-bicyclo[4.2.0]oct-2-ene-2-carboxylic acid benzhydryl ester
IR (KBr) 1783, 1720 cm$^{-1}$, MS (ISP) 653.4 (M+H)$^+$

EXAMPLE 5

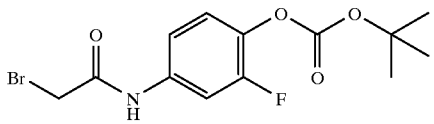

5.1. Carbonic acid 4-(2-bromoacetylamino)-2-fluoro-phenyl ester tert-butyl ester A solution of carbonic acid 4-amino-2-fluoro-phenyl ester tert-butyl ester (3 g, 13.2 mmol, synthesized according to Can. J. Chem. 63, 153 (1985)) and triethylamine (1.8 ml, 13.2 mmol) in 50 ml dichloromethane was treated with bromoacetylbromide (1.1 ml, 13.2 mmol) at 0–5° C. After 1 h, the reaction mixture was extracted with water, dried over magnesium sulfate and concentrated in vacuo. The oily residue was triturated with hexane, yielding 4.2 g (91%) of a beige solid.

IR(KBr) 1769 cm$^{-1}$; MS(EI) 348 (M+H)$^\bullet$.

According to the procedure set forth in the preceding example, the following additional compounds were prepared:

5.2. Carbonic acid 4-(2-bromo-acetylamino)-phenyl ester tert-butyl ester
5.3. Carbonic acid 3-(2-bromo-acetylamino)-phenyl ester tert-butyl ester
IR (KBr) 1751 cm$^{-1}$, MS (EI) 329 M$^\bullet$
5.4. Carbonic acid 2-(2-bromo-acetylamino)-phenyl ester tert-butyl ester
IR (KBr) 1770 cm$^{-1}$, MS (EI) 229 M$^\bullet$
5.5. Carbonic acid 4-(2-bromo-acetylamino)-3-fluoro-phenyl ester tert-butyl ester
IR (KBr) 1770, 1740 cm$^{-1}$, MS (ISP) 367.2 (M+NH$_4$)$^+$
5.6. Carbonic acid 4-(2-bromo-acetylamino)-2-chloro-phenyl ester tert-butyl ester
IR (KBr) 1770 cm$^{-1}$, MS (EI) 348 (M—CH$_3$)$^\bullet$
5.7. Carbonic acid 4-(2-bromo-acetylamino)-2-methoxy-phenyl ester tert-butyl ester
IR (KBr) 1759 cm$^{-1}$, MS (EI) 286 (M—OtBu)$^\bullet$
5.8. 2-Bromo-N-(3,4-difluoro-phenyl)-acetamide
IR (KBr) 1666 cm$^{-1}$, M (EI) 249 M$^\bullet$
5.9. 2-Bromo-N-(3-hydroxy-benzyl)-acetamide
IR (KBr) 1678 cm$^{-1}$, M (EI) 245 M$^\bullet$
5.10. 2-Bromo-N-[2-(tert-butyl-dimethyl-silanyloxy)-ethyl]-acetamide
IR (KBr) 1659 cm$^{-1}$, M (EI) 280 (M—CH$_3$)$^\bullet$
5.11. 2-Bromo-N-(5-methyl-1,3,4-thiadiazol-2-yl)-acetamide
IR (KBr) 1606 cm$^{-1}$, MS (EI) 235 M$^\bullet$
5.12. 2-Bromo-N-(4-methoxy-phenyl)-acetamide
5.13. 2-Bromo- 1-(2,3-dihydro-indol-1-yl)-ethanone
IR (KBr) 1660 cm$^{-1}$, MS (EI) 239 M$^\bullet$
5.14. N-(3-Acetylamino-4-hydroxy-phenyl)-2-bromo-acetamide
5.15. (R)-3-(2-Bromo-acetylamino)-pyrrolidine-1-carboxylic acid allyl ester
IR (KBr) 1674 cm$^{-1}$, MS (ISP) 308.1 (M+NH$_4$)$^+$

EXAMPLE 6 preparation (6) ⟶ (7), scheme 1

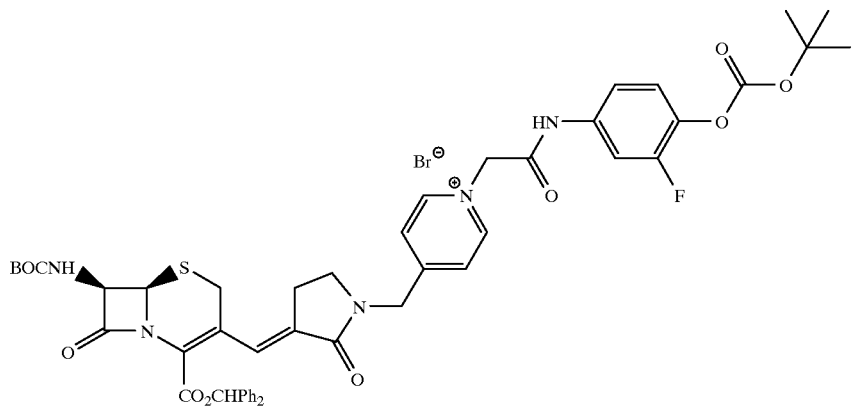

6.1. (E)-(6R,7R)4-[(2-Benydryloxycarbonyl-7-tert-butoxycabonylamino8-oxo-5-thia-1-bicyclo[4.2.0]oct2-en-3-ylmethylene)-2-oxo-pyrrolidin-1-ylmethyl]-1-[(4-tert-butoxycarbonyloxy-3-fluoro-phenylcarbamoyl)-methyl]-pyridinium bromide (E )-(6R,7R)-7-tert-Butoxycarbonylamino-8-oxo-(2-oxo-1-pyridin-4-ylmethylpyrrolidin-3-ylidenemethyl)-5-thia-1-aza-bicyclo[4.2.0]oct-2-ene-2-carboxylic acid benzhydryl ester (1 g, 1.53 mmol) in 25 ml DMF was treated with carbonic acid 4-(2-bromo-acetylamino)-2-fluoro-phenyl ester tert-butyl ester (1.06 g, 3.00 mmol) for 25 h at room temperature. The solvent was removed in vacuo and the residue was triturated with diethylether yielding 1.1 g (72%) of the product as a beige powder.

IR(KBr) 1770, 1698 cm$^{-1}$; MS(ISP) 920.5 M$^+$.

According to the procedure set forth in the preceding example, the following additional compounds were prepared:

6.2. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-tert-butoxycarbonyloxy-phenylcarbamoyl)-methyl]-pyridinium bromide IR (KBr) 1783, 1758 cm$^{-1}$, MS (ISP) 902.6 (M+H)$^+$ 6.3. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(3-tert-butoxycarbonyloxy-phenylcarbamoyl)-methyl]-pyridinium bromide IR (KBr) 1781, 1761 cm$^{-1}$, MS (ISP) 902.5 M$^+$ 6.4. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(2-tert-butoxycarbonyloxy-phenylcarbamoyl)-methyl]-pyridinium bromide IR (KBr) 1779, 1712 cm$^{-1}$, MS (ISP) 902.6 M$^+$ 6.5. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-tert-butoxycarbonyloxy-2-fluoro-phenylcarbamoyl)-methyl]-pyridinium bromide IR (KBr) 1781, 1712 cm$^{-1}$, MS (ISP) 920.5 M$^+$ 6.6. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-tert-butoxycarbonyloxy-3-chloro-phenylcarbamoyl)-methyl]-pyridinium bromide IR (KBr) 1772, 1701 cm$^{-1}$, MS (ISP) 936.5 M$^+$ 6.7. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-tert-butoxycarbonyloxy-3-methoxy-phenylcarbamoyl)-methyl]-pyridinium bromide IR (KBr) 1783, 1770 cm$^{-1}$, MS (ISP) 932.5 M$^+$ 6.8. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(3,4-difluoro-phenylcarbamoyl)-methyl]-pyridinium bromide IR (KBr) 1783, 1697 cm$^{-1}$, MS (ISP) 822.4 M$^+$ 6.9. (E)-(6R,7R)-4-[3-(2-Benzhydryloxycarbonyl-7-tert-butoxyearbonylamino-8-oxo-5-thia-1-aza-bicyclo[4.2.0] oct-2-en-3-ylmethylene)-2-oxo-pyrrolidin-1-ylmethyl]-1-[(3-hydroxy-benzylcarbamoyl)-methyl]-pyridinium bromide IR (KBr) 1781, 1691 cm$^{-1}$, MS (ISP) 816.5 M$^+$ 6.10. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[[2-(tert-butyl-dimethyl-silanyloxy)-ethylcarbamoyl]-methyl]-pyridinium bromide IR (KBr) 1784, 1718 cm$^{-1}$, MS (ISP) 868.6 M$^+$ 6.11. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(5-methyl-[1,3,4]thiadiazol-2-ylcarbamoyl)-methyl]-pyridinium bromide IR (KBr) 1783, 1712 cm$^{-1}$, MS (ISP) 808.3 (M+H)$^+$ 6.12. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-methoxy-phenylcarbamoyl)-methyl]-pyridinium bromide IR (KBr) 1789, 1716 cm$^{-1}$, MS (ISP) 816.5 M$^+$ 6.13. (E)-(6R,7R)-4-[3-(2-Benzhydryloxyearbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[2-(2,3-dihydro-indol-1-yl)-2-oxo-ethyl]-pyridinium bromide IR (KBr) 1782, 1717 cm$^{-1}$, MS (ISP) 812.6 M$^+$ 6.14. (E)-(6R,7R)-1-[(1-Allyloxycarbonyl-pyrrolidin-3-ylcarbamoyl)-methyl]-4-[3-(2-benzhydryloxycarbonyl-7-tert-butoxycarbonylamino-8-oxo-5-thia-1-aza-bicyclo [4.2.0]oct-2-en-3-ylmethylene)-2-oxo-pyrrolidin-1-ylmethyl]-pyridinium bromide IR (KBr) 1783, 1687 cm$^{-1}$, MS (ISP) 863.5 M$^+$ 6.15. (E )-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-methyl-pyridinium sulfate IR (KBr) 1778, 1714 cm$^{-1}$, MS (ISP) 667.5 (M)$^+$ 6.16. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-carbamoylmethyl-pyridinium bromide IR (KBr) 1780, 1695 cm$^{-1}$, MS (ISP) 710.4 (M+H)$^+$ 6.17. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-benzyl-pyridinium bromide IR (KBr) 1781, 1717 cm$^{-1}$, MS (ISP) 743.4 M$^+$ 6.18. (E )-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-(4-cyano-benzyl)-pyridinium bromide IR (KBr) 1781, 1717 cm$^{-1}$, MS (ISP) 768.4 M$^+$ 6.19. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-(3-hydroxy-benzyl)-pyridinium bromide IR (KBr) 1781, 1717 cm$^{-1}$, MS (ISP) 759.2 (M+H)$^+$ 6.20. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-(4-carboxy-benzyl)-pyridinium bromide IR (KBr) 1781, 1715 cm$^{-1}$, MS (ISP) 787.4 M$^+$ 6.20a. (E)-(6R,7R)-4-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-tert-butoxycarbonyloxy-2-trifluoromethyl-phenylcarbamoyl)-methyl]-pyridinium bromide IR (KBr): 1780, 1766 cm$^{-1}$, MS (ISP) 970,5 M$^+$ The following compounds were prepared in the same way using (E)-(6R,7R)-7-tert-butoxycarbonylamino-8-oxo-3-(2-oxo-1-pyridin-3-ylmethyl-pyrrolidin-3-ylidenemethyl)-5-thia-1-aza-bicyclo[4.2.0]oct-2-ene-2-carboxylic acid benzhydryl ester 6.21. (E)-(6R,7R)-3-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(5-methyl-[1,3,4]thiadiazol-2-ylcarbamoyl)-methyl]-pyridinium bromide IR (KBr) 1771, 1713 cm$^{-1}$, MS (ISP) 920.5 M$^+$ 6.22. (E)-(6R,7R)-3-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(3-tert-butoxycarbonyloxy-phenylcarbamoyl)-methyl]-pyridinium bromide IR (KBr) 1784, 1714 cm$^{-1}$, MS (ISP) 902.7 M$^+$ 6.23. (E)-(6R,7R)-3-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin- 1-ylmethyl]-1-[(4-tert-butoxycarbonyloxy-phenylcarbamoyl)-methyl]-pyridinium bromide IR (KBr) 1784, 1759 cm$^{-1}$, MS (ISP) 902.5 M$^+$ 6.24. (E)-(6R,7R)-3-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-[(4-tert-butoxycarbonyloxy-3-fluoro-phenylcarbamoyl)-methyl]-pyridinium bromide IR (KBr) 1783, 1716 cm$^{-1}$, MS (ISP) 808.4 M$^+$ The following compound was prepared in the same way using (E)-(6R,7R)-7-tert-butoxycarbonylamino-8-oxo-3 -(2-oxo-1-pyridin-2-ylmethyl-pyrrolidin-3-ylidenemethyl)-5-thia-1-aza-bicyclo[4.2.0]oct-2-ene-2-carboxylic acid benzhydryl ester 6.25. (E)-(6R,7R)-2-[3-(2-Benzhydryloxycarbonyl-7-tert-butoxycarbonylamino-8-oxo-5-thia-1-aza-bicyclo[4.2.0] oct-2-en-3-ylmethylene)-2-oxo-pyrrolidin-1-ylmethyl]-1-methyl-pyridinium tetrafluoroborate IR (KBr) 1782, 1716 cm$^{-1}$, MS (ISP) 667.3 (M+H)$^+$

EXAMPLE 7 preparation (7) ⟶ (8), scheme 1

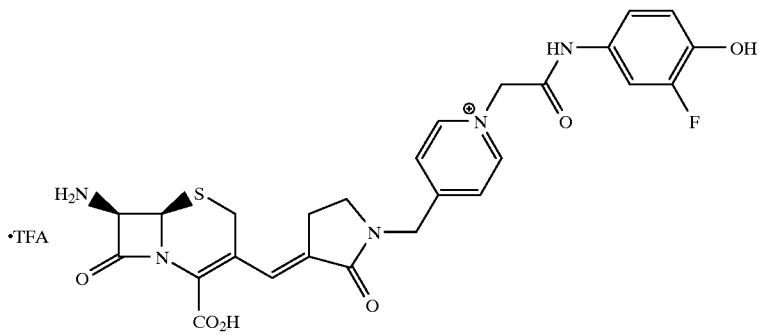

7.1. (E)-(6R,7R)-7-Amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt A solution of (E)-(6R,7R)-4-[3-(2-benzhydryloxycarbonyl-7-tert-butoxycarbonylamino-8-oxo-5-thia-1-aza-bicyclo[4.2.0]oct-2-en-3-ylmethylene)-2-oxo-pyrrolidin-1-ylmethyl]-1-[(4-tert-butoxycarbonyloxy-3-fluoro-phenylcarbamoyl)-methyl]-pyridinium bromide (1.1 g, 1.09 mmol) in 25 ml dichloromethane was treated with 1.2 ml anisol and 5 ml trifluoroacetic acid at 0–5° C. After 3 h stirring at room temperature, the mixture was concentrated and triturated with diethylether yielding 697 mg (96%) of a beige solid.

IR(KBr) 1782, 1678 cm$^{-1}$; MS(ISP) 554.3 (M+H)$^+$.

According to the procedure set forth in the preceding example, the following additional compounds were prepared:

7.2. (E)-(6R,7R)-7-Amino-3-[1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1782, 1678 cm$^{-1}$, MS (ISP) 558.2 (M+Na$^+$)

7.3. (E)-(6R,7R)-7-Amino-3-[1-[1-[(3-hydroxy-phenylcarbamoyl)-methyl]-pyridin-1-ium-4-ylmethyl]-2-oxo-pyrrolidin-3-ylidenemethyl]8-oxo-5-thia-1-aza-bicyclo[4.2.0]oct-2-ene-2-carboxylate trifluoro-acetic acid salt IR (KBr) 1781, 1680 cm$^{-1}$, MS (ISP) 536.3 (M+H)$^+$ 7.4. (E)-(6R,7R)-7-Amino-3-[1-[1-[(2-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1782, 1679 cm$^{-1}$, MS (ISP) 536.3 (M+H)$^+$ 7.5. (E)-(6R,7R)-7-Amino-3-[1-[1-[(2-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1785, 1680 cm$^{-1}$, MS (ISP) 554.2 (M+H)$^+$ 7.6. (E )-(6R,7R)-7-Amino-3-[1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1783, 1689 cm$^{-1}$, MS (ISP) 570.2 (M+H)$^+$ 7.7. (E)-(6R,7R)-7-Amino-3-[1-[1-[(4-hydroxy-3-methoxy-phenylcarbamoyl)-methyl]-pyridin-1-ium-$^{-4}$-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1782, 1679 cm$^{-1}$, MS (ISP) 566.3 (M+H)$^+$ 7.8. (E)-(6R,7R)-7-Amino-3-[1-[1-[(3,4-difluoro-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1780, 1682 cm$^{-1}$, MS (ISP) 556.1 (M+H)$^+$ 7.9. (E)-(6R,7R)-7-Amino-3-[1-[1-[(3-hydroxy-benzylcarbamoyl)-methyl]-pyridin-1-ium-4-ylmethyl]-2-oxo-pyrrolidin-3-ylidenemethyl]-8-oxo-5-thia- 1-aza-bicyclo[4.2.0]oct-2-ene-2-carboxylate trifluoroacetic acid salt IR (KBr) 1783, 1681 cm$^{-1}$, MS (ISP) 550.4 (M+H)$^+$ 7.10. (E)-(6R,7R)-7-Amino-3-[1-[1-[(2-hydroxy-ethylcarbamoyl)-methyl]-pyridin-1-ium-4-ylmethyl]-2-oxo-pyrrolidin-3-ylidenemethyl]-8-oxo-5-thia- 1-aza-bicyclo [4.2.0]oct-2-ene-2-carboxylate trifluoroacetic acid salt IR (KBr) 1783, 1680 cm$^{-1}$, MS (ISP) 488.4 (M+H)$^+$ 7.11. (E)-(6R,7R)-7-Amino-3-[1-[1-[(5-methyl-[1,3,4]thiadiazol-2-ylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1781, 1681 cm$^{-1}$, MS (ISP) 542.3 (M+H)$^+$ 7.12. (E)-(6R,7R)-7-Amino-3-[1-[1-[(4-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoro-acetic acid salt IR (KBr) 1783, 1681 cm$^{-1}$, MS (ISP) 550.2 (M+H)$^+$ 7.13. (E)-(6R,7R)-7-Amino-3-[1-[1-[2-(2,3-dihydro-indol-1-yl)-2-oxo-ethyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1783, 1675 cm$^{-1}$, MS (ISP) 546.3 (M+H)$^+$ 7.14. (E)-(6R,7R)-3-{1-(1-[(1-Allyloxycarbonyl-3-methyl-pyrrolidin-3-ylcarbamoyl)-methyl]-pyridin-1-ium-4-ylmethyl}-2-oxo-pyrrolidin-3-ylidenemethyl)-7-amino-8-oxo-5-thia-1-aza-bicyclo[4.2.0]oct-2-ene-2-carboxylate trifluoroacetic acid salt IR (KBr) 1790, 1691 cm$^{-1}$, MS (ISP) 597.2 (M+H)$^+$ 7.15. (E)-(6R,7R)-7-Amino-3-[1-(1-methyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate trifluoro-acetic acid salt IR (KBr) 1784, 1677 cm$^{-1}$, MS (ISP) 401.3 M$^+$ 7.16. (E)-(6R,7R)-7-Amino-3-[1-(1-carbamoylmethyl-pyridin-1-ium-4-ylmethyl)-2-oxo-pyrrolidin-3-ylidenemethyl-8-oxo-5-thia-1-aza-bicyclo[4.2.0]oct-2-ene-2-carboxylate trifluoroacetic acid salt IR (KBr) 1779, 1683 cm$^{-1}$, MS (ISP) 444.4 M$^+$ 7.17. (E)-(6R,7R)-7-Amino-3-[1-(1-benzyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylatetrifluoroacetic acid salt IR (KBr) 1782, 1690 cm$^{-1}$, MS (ISP) 477.3 (M+H)$^+$ 7.18. (E)-(6R,7R)-7-Amino-3-[1-[1-(4-cyano-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1781, 1679 cm$^{-1}$, MS (ISP) 502.0 (M+H)$^+$ 7.19. (E)-(6R,7R)-7-Amino-3-[1-[1-(3-hydroxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1774, 1676 cm$^{-1}$, MS (ISP) 493.3 (M+H)$^+$ 7.20. (E)-(6R,7R)-7-Amino-3-[1-[1-(4-carboxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1780, 1680 cm$^{-1}$, MS (ISP) 543.3 (M+Na$^+$)

7.21. (E)-(6R,7R)-7-Amino-3-[1-[1-[(2-methyl-benzooxazol-5-ylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1764, 1679 cm$^{-1}$, MS (ISP) 575.3 (M+H)$^+$ 7.22. (E)-(6R,7R)-7-Amino-3-[1-[1-(2-hydroxy-ethyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1778, 1678 cm$^{-1}$, MS (ISP) 453.3 (M+Na$^+$)

7.23. (E)-(6R,7R)-7-Amino-3-[1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1782, 1680 cm$^{-1}$, MS (ISP) 554.1 (M+H)$^+$ 7.24. (E)-(6R,7R)-7-Amino-3-[1-[1-[(4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1780, 1670 cm$^{-1}$, MS (ISP) 558.1 (M+Na$^+$)

7.25. (E)-(6R,7R)-7-Amino-3-[1-[1-[(3-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1781, 1680 cm$^{-1}$, MS (ISP) 536.2 (M+H)$^+$ 7.26. (E)-(6R,7R)-7-Amino-3-[1-[1-[(5-methyl-[1,3,4]thiadiazol-2-ylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1783, 1679 cm$^{-1}$, MS (ISP) 564.1 (M+Na$^+$)

7.27. (E)-(6R,7R)-7-Amino-3-[1-[1-[(4-hydroxy-phenylcarbamoyl)-methyl]-pyridin-1-ium-2-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1780, 1681 cm$^{-1}$, MS (ISP) 536.3 (M+H)$^+$ 7.28. (E)-(6R,7R)-7-Amino-3-[1-[1-(3-hydroxy-benzyl)-pyridin-1-ium-2-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1784, 1677 cm$^{-1}$, MS (ISP) 493.3 (M+H)$^+$ 7.29. (E )-(6R,7R)-7-Amino-3-[1-(1-methyl-pyridin-1-ium-2-ylmethyl)-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1782, 1680 cm$^{-1}$, MS (ISP) 401.2 (M+H)$^+$ 7.30. (E)-(6R,7R)-7-Amino-3-[1-[1-[(4-hydroxy-2-trifluoromethyl-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetate (1:1)

IR (KBr): 1782, 1679 cm$^{-1}$, MS(ISP): 604.2 (M+H$^+$)

EXAMPLE 8 preparation (8) ⟶ (10), scheme 1

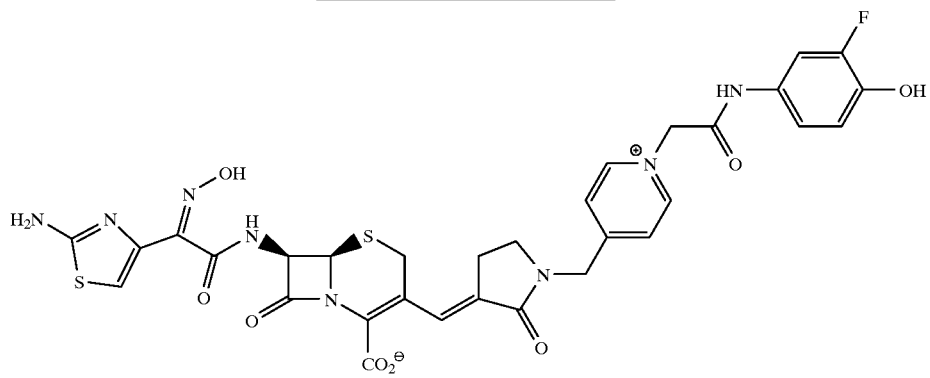

8.1. (6R,7R)-7-[(Z)-2-(2-Amino-thiazol-4-yl)-2-hydroxyimino-acetylamino]-3-[(E)-1-[1-(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate A suspension of (E)-(6R,7R)-7-amino-3-[1-[1-[(3-fluoro-4-hydroxyphenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt (400 mg, 0.72 mmol) ) in 10 ml DMF was treated with (Z)-(2-aminothiazol-4-yl)-trityloxyimino-acetic acid 1-benzotriazolyl ester (394 mg, 0.72 mmol) for 24 h at room temperature. The reaction mixture was concentrated in vacao and the residue triturated with ethyl acetate yielding 461 mg (60%) of a beige solid. The solid was treated with 3 ml trifluoroacetic acid and triethylsilane (0.2 ml, 0.85 mmol) at 0–5° C. for 30 min. The reaction mixture was added dropwise into diethylether upon which the product separated as a beige solid. It was purified by gel chromatography (MCI Gel 75–150μ, using a gradient of water with increasing concentrations of acetonitrile). Yield: 380 mg (28%).

IR(KBR) 1767, 1672 $cm^{-1}$; MS(ISP) 723.4 $(M+H)^+$.

According to the procedure set forth in the preceding example, the following additional compounds were prepared:

8.2. (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyrdin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1766 $cm^{-1}$, MS (ISP) 727.4 $(M+Na^+)$ 8.3. (6R,7R)-7-[(Z)-2-(2-Amino-thiazol-4-yl)-2-hydroxyimino-acetylamino]-3-[(E)-1-[1-[(3-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1765, 1665 $cm^{-1}$, MS (ISP) 705.3 $(M+H)^+$ 8.4. (6R,7R)-7-[(Z)-2-(2-Amino-thiazol-4-yl)-2-hydroxyimino-acetylamino]-3-[(E)-1-[1-[(2-hydroxy-phenylcarbamoyl)-methyl]-pyridin-1-ium-4-ylmethyl]-2-oxo-pyrrolidin-3-ylidenemethyl)-8-oxo-5-thia-1-aza-bicyclo[4.2.0]oct-2-ene-2-carboxylate IR (KBr) 1770, 1669 $cm^{-1}$, MS (ISP) 705.3 $(M+H)^+$ 8.5. (6R,7R)-7-[(Z)-2-(2-Amino-thiazol-4-yl)-2-hydroxyimino-acetylamino]-3-[(E)-1-[1-[(2-fluoro-4-hydroxy-phenylcarbamoyl)-methyl]-pyridin-1-ium-4-ylmethyl]-2 -oxo-pyrrolidin-3-ylidenemethyl]-8-oxo-5-thia-1 -aza-bicyclo[4.2.0]oct-2-ene-2-carboxylate IR (KBr) 1765, 1625 $cm^{-1}$, MS (ISP) 723.3 $(M+H)^+$ 8.6. (6R,7R)-7-[(Z)-2-(2-Amino-thiazol-4-yl)-2-hydroxyimino-acetylamino]-3-[(E)-1-[(3-chloro-4-hydroxy-phenylcarbamoyl)-methyl-pyridin-1-ium-4-ylmethyl]-2-oxo-pyrrolidin-3-ylidenemethyl]-8-oxo-5-thia-1-aza-bicyclo-[4.2.0]oct-$^2$-ene-2-carboxylate IR (KBr) 1766, 1675 $cm^{-1}$, MS (ISP) 739.2 $(M+H)^+$ 8.7. (6R,7R)-7-[(Z)-2-(2-Amino-thiazol-4-yl)-2-hydroxyimino-acetylamino]-3-[(E)-1-[1-[(4-hydroxy-3-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo-[4.2.0]oct-2-ene-2-carboxylate IR (KBr) 1769, 1671 $cm^{-1}$, MS (ISP) 735.5 $(M+H)^+$ 8.8. (6R,7R)-7-[(Z)-2-(2-Amino-thiazol-4-yl)-2-hydroxyimino-acetylamino]-3-[(E)-1-[1-[(3,4-difluoro-phenylcarbamoyl)-methyl-]pyridin-1-ium-4-ylmethyl]-2-oxo-pyrrolidin-3-ylidenemethyl]-8-oxo-5-thia- 1-aza-bicyclo[4.2.0]oct-2-ene-2-carboxylate IR (KBr) 1766, 1675 $cm^{-1}$, MS (ISP) 725.0 $(M+H)^+$ 8.9. (6R,7R)-7-[(Z)-2-(2-Amino-thiazol-4-yl)-2-hydroxyimino-acetylamino]-3-[(E)-1-[1-[(3-hydroxy-benzylcarbamoyl)-methyl]-pyridin-1-ium-4-ylmethyl]-2-oxo-pyrrolidin-3-ylidenemethyl]-8-oxo-5-thia-1-aza-bicyclo [4.2.0]oct-2-ene-2-carboxylate IR (KBr) 1766, 1688 $cm^{-1}$, MS (ISP) 657.3 $(M+H)^+$ 8.10. (6R,7R)-7-[(Z)-2-(2-Amino-thiazol-4-yl)-2-hydroxyimino-acetylamino]-3-[(E)-1-[1-[(2-hydroxy-ethylcarbamoyl)-methyl]-pyridin-1-ium-4-ylmethyl]-2-oxo-pyrrolidin-3-ylidenemethyl]-8-oxo-5-thia-1-aza-bicyclo [4.2.0]oct-2-ene-2-carboxylate IR (KBr) 1769, 1675 $cm^{-1}$, MS (ISP) 719.3 $(M+H)^+$ 8.11. (6R,7R)-7-[(Z)-2-(2-Amino-thiazol-4-yl)-2-hydroxyimino-acetylamino]-3-[(E)-1-[1-(5-methyl-[1,3,4]thiadiazol-2-ylcarbamoyl)-methyl]-pyridin-1-ium-4-ylmethyl]-2-oxo-pyrrolidin-3-ylidenemethyl]-8-oxo-5-thia-1-aza-bicyclo-[4.2.0]oct-2-ene-2-carboxylate IR (KBr) 1766, 1665 $cm^{-1}$, MS (ISP) 711.3 $(M+H)^+$ 8.12. (6R,7R)-7-[(Z)-2-(2-Amino-thiazol-4-yl)-2-hydroxyimino-acetylamino]-3-[(E)-1-[1-[(4-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1770, 1680 $cm^{-1}$, MS (ISP) 719.4 $(M+H)^+$ 8.13. (6R,7R)-7-[(Z)-2-(2-Amino-thiazol-4-yl)-2-hydroxyimino-acetylamino]-3-[(E)-1-[1-[2-(2,3-dihydro-indol-1-yl)-2-oxo-ethyl]-pyridin-1-ium-4-ylmethyl]-2-oxo-pyrrolidin-3-ylidenemethyl]-8-oxo-5-thia-1-aza-bicyclo [4.2.0]oct-2-ene-2-carboxylate IR (KBr) 1771, 1670 $cm^{-1}$, MS (ISP) 715.4 $(M+H)^+$ 8.14. (6R,7R)-7-[(Z)-2-(2-Amino-thiazol-4-yl)-2-hydroxyimino-acetylamino]-3-[(E )-1-(1-methyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate IR (KBr) 1767, 1666 $cm^{-1}$, MS (ISP) 592.3 $(M+Na^+)$ 8.15. (6R,7R)-7-[(Z)-2-(2-Amino-thiazol-4-yl)-2-hydroxyimino-acetylamino]-3-[(E)-1-(1-carbamoylmethyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate IR (KBr) 1764, 1672 $cm^{-1}$, MS (ISP) 613.3 $(M+H)^+$ 8.16. (6R,7R)-7-[(Z)-2-(2-Amino-thiazol-4-yl)-2-hydroxyimino-acetylamino]-3-[(E)-1-(1-benzyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate IR (KBr) 1768, 1639 $cm^{-1}$, MS (ISP) 646.4 $(M+H)^+$ 8.17. (6R,7R)-7-[(Z)-2-(2-Amino-thiazol-4-yl)-2-hydroxyimino-acetylamino]-3-[(E)-1-[1-(4-cyano-benzyl)-pyridin-1-ium-4-ylmethyl]-2-oxo-pyrrolidin-3-ylidenemethyl]-8-oxo-5-thia- 1-aza-bicyclo[4.2.0]oct-2-ene-2-carboxylate IR (KBr) 1775, 1677 $cm^{-1}$, MS (ISP) 671.3 $(M+H)^+$ 8.18. (6R,7R)-7-[(Z)-2-(2-Amino-thiazol-4-yl)-2-hydroxyimino-acetylamino]-3-[(E)-1-[1-(3-hydroxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1774, 1676 $cm^{-1}$, MS (ISP) 662.3 $(M+H)^+$ 8.19. (6R,7R)-7-[(Z)-2-(2-Amino-thiazol-4-yl)-2-hydroxyimino-acetylamino]-3-[(E)-1-[1-(4-carboxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate sodium salt IR (KBr) 1767, 1694 $cm^{-1}$, MS (ISP) 690.2 $(M+H)^+$ 8.20. (6R,7R)-7-[(Z)-2-(2-Amino-thiazol-4-yl)-2-hydroxyimino-acetylamino]-3-[(E)-1-[1-[(2-methyl-benzooxazol-5-ylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1766, 1668 $cm^{-1}$, MS (ISP) 744.6 $(M+H)^+$ 8.21. (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate IR (KBr) 1767, 1668 cm$^{-1}$, MS (ISP) 723.4 (M+H)$^+$ 8.22. (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate IR (KBr) 1766, 1671 cm$^{-1}$, MS (ISP) 705.2 (M+H)$^+$ 8.23. (6R, 7R)-7-[(Z)-2-(2-Amino-thiazol-4-yl)-2-hydroxyimino-acetylamino]-3-[(E)-1-[1-[(3-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate IR (KBr) 1766, 1664 cm$^{-1}$, MS (ISP) 705.3 (M+H)$^+$ 8.24. (6R,7R)-7-[(Z)-2-(2-Amino-thiazol-4-yl)-2-hydroxyimino-acetylamino]-3-[(E)-1-[1-[(5-methyl-[1,3,4]thiadiazol-2-ylcarbamoyl)-methyl]-pyridin-1-ium-3-ylmethyl-2-oxo-pyrrolidin-3-ylidenemethyl]-8-oxo-5-thia-1-aza-bicyclo-[4.2.0]oct-2-ene-2-carboxylate IR (KBr) 1766, 1669 cm$^{-1}$, MS (ISP) 711.2 (M+H)$^+$ 8.25. (6R,7R)-7-[(Z)-2-(2-Amino-thiazol-4-yl)-2-hydroxyimino-acetylamino]-3-[(E)-1-[1-(3-hydroxy-benzyl)-pyridin-1-ium-2-ylmethyl]-2-oxo-pyrrolidin-3-ylidenemethyl]-8-oxo-5-thia-1-aza-bicyclo[4.2.0]oct-2-ene-2-carboxylate IR (KBr) 1771, 1672 cm$^{-1}$, MS (ISP) 662.2 (M+H)$^+$ 8.26. (6R,7R)-7-[(Z)-2-(2-Amino-thiazol-4-yl)-2-hydroxyimino-acetylamino]-3-[(E)-1-(1-methyl-pyridin-1-ium-2-ylmethyl)-2-oxo-pyrrolidin-3-ylidenemethyl]-8-oxo-5-thia-1-aza-bicyclo[4.2.0]oct-2-ene-2-carboxylate IR (KBr) 1775, 1678 cm$^{-1}$, MS (ISP) 570.1 (M+H)$^+$ 8.27 (6R,7R)-7-[(Z)-2-(2-Amino-thiazol-4-yl)-2-hydroxyimino-acetylamino]-3-[(E)-1-[1-[(4-hydroxy-2-trifluoromethyl-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1672 cm$^{-1}$, MS (ISP) 773.4 (M+H$^+$)

EXAMPLE 9

9.1. (6R,7R)-7-[(Z)-2-(5-Amino-[1,2,4]thiadiazol-3-yl)-2-hydroxyiminoacetylamino]3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate A suspension of (E)-(6R,7R)-7-amino-3-[1-[1-[(3-fluoro-4-hydroxyphenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt (500 mg, 0.74 mmol) ) in 20 ml DMF was treated with (Z)-(5-amino-[1,2,4]thiadiazol-3-yl)-trityloxyimino-thioacetic acid 2-mercaptobenzothiazolyl ester (434 mg, 0.74 mmol) for 21 h at room temperature. The reaction mixture was concentrated in vacuo and the residue triturated with ethyl acetate and diethylether. The solid was treated with 5 ml trifluoroacetic acid and triethylsilane (0.2 ml, 1.06 mmol) at 0–5° C. for 30 min. The reaction mixture was added dropwise into diethylether upon which the product separated as a beige solid. It was purified by gel chromatography (MCI Gel 75–150μ, using a gradient of water with increasing concentrations of acetonitrile). Yield: 182 mg (47%).

IR(KBr) 1767, 1673 cm$^{-1}$; MS(ISP) 724.2 (M+H)$^+$.

According to the procedure set forth in the preceding example, the following additional compounds were prepared:

9.2. (6R,7R)-7-[(Z)-2-(5-Amino-[1,2,4]thiadiazol-3-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]-oct-2-ene-2-carboxylate IR (KBr) 1780, 1671 cm$^{-1}$, MS (ISP) 706.3 (M+H)$^+$ preparation (8) ⟶ (10), scheme 1

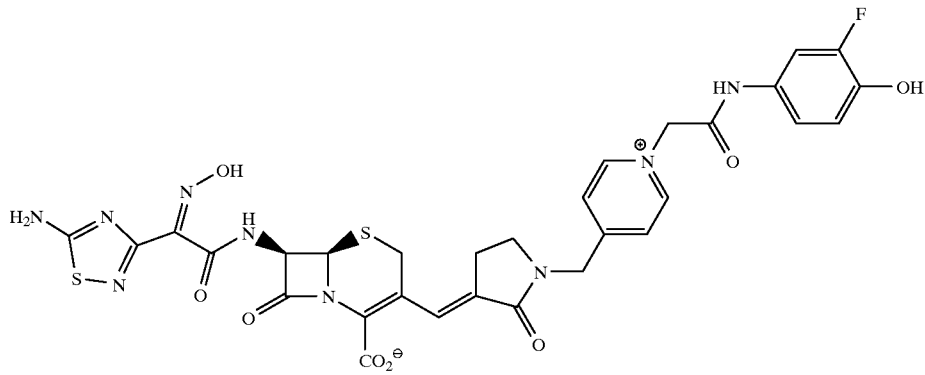

EXAMPLE 10

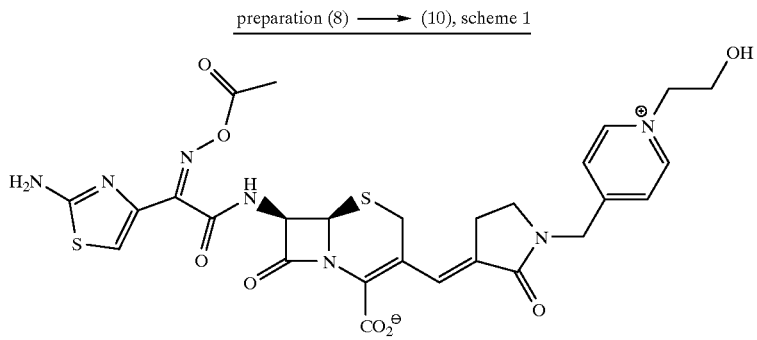

(6R,7R)-7-[(Z)-2-Acetoxyimino-2-(2-amino-thiazol-4-yl)-acetylamino]-3-[(E)-1-[1-(2-hydroxy-ethyl)-pyridin-1-ium-1-ylmethyl]-2-oxo-pyrrolidin-3-ylidenemethyl]-8-oxo-5-thia-1-aza-bicyclo[4.2.0]oct-2-ene-2-carboxylate A solution of (E)-(6R,7R)-7-amino-3-[1-[1-(2-hydroxy-ethyl)-pyridin-1-ium-4-ylmethyl]-2-oxo-pyrrolidin-3-ylidenemethyl]-8-oxo-5-thia- 1-aza-bicyclo[4.2.0]oct-2-ene-2-carboxylate trifluoroacetic acid salt (600 mg, 1.1 mmol) in 20 ml DMF was treated with (Z)-(2-amino-thiazol-4-yl)-acetoxyimino-acetic acid diethoxy-thiophosphoryl ester (420 mg, 1.1 mmol) for 24 h at room temperature. The reaction mixture was concentrated in vacuo and the residue triturated with ethyl acetate. The resulting solid was purified by gel chromatography (MCI Gel 75–150µ, using a gradient of water with increasing concentrations of acetonitrile). Yield: 67 mg (9%). IR(KBr) 1768, 1669 cm$^{-1}$; MS(ISP) 664.2 (M+Na)$^+$.

EXAMPLE 11

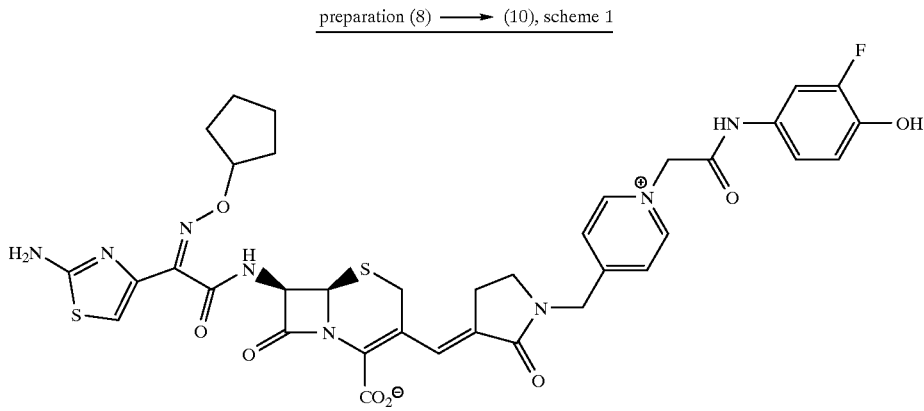

11.1. (6R,7R)-7-[(Z)-2-(2-Amino-thiazol-4-yl)-2-cyclopentyloxyiminoacetylamino]-3-[(E)-1-[1-[(3-fluoro-4-hydroxy-phenylcarbamoyl)-methyl]-pyridin-1ium-4-ylmethyl]-2-oxo-pyrrolidin-3-ylidenemethyl]-8-oxo-5-thia-1-aza-bicyclo[4.2.0]oct-2-ene-2-carboxylate A suspension of (E)-(6R,7R)-7-amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt (180 mg, 0.26 mmol) ) in 5 ml DMF was treated with (Z)-(2-aminothiazol-4-yl)-cyclopentyloxyimino-acetic acid 2-mercaptobenzothiazolyl ester (109 mg, 0.72 mmol) for 24 h at room temperature. The reaction mixture was concentrated in vacuo and the residue triturated with ethyl acetate. The resulting solid was purified by reversed phase chromatography (MERCK Lichroprep RP-18 silica gel, 25–40µ, using a gradient of water with increasing concentrations of acetonitrile). Yield: 64 mg (31%).

IR(KBr) 1768, 1671 cm$^{-1}$; MS(ISP) 791.3 (M+H)$^+$.

According to the procedure set forth in the preceding example, the following additional compounds were prepared:

11.2. ($^6$R,7R)-7-[(Z)-2-(2-Amino-thiazol-4-yl)-2-cyclopentyloxyimino-acetylamino]-3-[(E )-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1674 cm$^{-1}$, MS (ISP) 773.4 (M+H)$^+$ 11.3. (6R,$^7$R)-7-[(Z)-2-(2-Amino-thiazol-4-yl)-2-cyclopentyloxyimino-acetylamino]-3-[(E)-1-[1-[(3-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1770, 1677 cm$^{-1}$; MS (ISP) 773.3 (M+H)$^+$ 11.4. (6R,7R)-7-[(Z)-2-(2-Amino-thiazol-4-yl)-2-cyclopentyloxyimino-acetylamino]-3-[(E)-1-[1-[(2-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1676 cm$^{-1}$; MS (ISP) 773.4 (M+H)$^+$ 11.5. (6R,7R)-7-[(Z)-2-(2-Amino-thiazol-4-yl)-2-cyclopentyloxyimino-acetylamino]-3-[(E)-1-[1-[(2-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1767, 1673 cm$^{-1}$; MS (ISP) 791.4 (M+H)$^+$ 11.6. (6R,7R)-7-[(Z)-2-(2-Amino-thiazol-4-yl)-2-cyclopentyloxyimino-acetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1775, 1680 cm$^{-1}$; MS (ISP) 807.3 (M+H)$^+$ 11.7. (6R,7R)-7-[(Z)-2-(2-Amino-thiazol-4-yl)-2-cyclopentyloxyimino-acetylamino]-3-[(E)-1-[1-[(4-hydroxy-3-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1672 cm$^{-1}$; MS (ISP) 803.4 (M+H)$^+$ 11.8. (6R,7R)-7-[(Z)-2-(2-Amino-thiazol-4-yl)-2-cyclopentyloxyimino-acetylamino]-3-[(E)-1-[1-[(3,4-difluoro-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1770, 1673 cm$^{-1}$; MS (ISP) 793.3 (M+H)$^+$ 11.9. (6R,7R)-7-[(Z)-2-(2-Amino-thiazol-4-yl)-2-cyclopentyloxyimino-acetylamino]-3-[(E)-1-[1-[(3-hydroxy-benzylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1768, 1674 cm$^{-1}$; MS (ISP) 787.7 (M+H)$^+$ 11.10. (6R,7R)-7-[(Z)-2-(2-Amino-thiazol-4-yl)-2-cyclopentyloxyimino-acetylamino]-3-[(E)-1-[1-[(2-hydroxy-ethylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1778, 1675 cm$^{-1}$; MS (ISP) 725.5 (M+H)$^+$ 11.11. (6R,7R)-7-[(Z)-2-(2-Amino-thiazol-4-yl)-2-cyclopentyloxyimino-acetylamino]-3-[(E)-1-[1-[(5-methyl-[1,3,4]thiadiazol-2-ylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1780, 1675 cm$^{-1}$; MS (ISP) 779.5 (M+H)$^+$ 11.12. (6R,7R)-7-[(Z)-2-(2-Amino-thiazol-4-yl)-2-cyclopentyloxyimino-acetylamino]-3-[(E)-1-[1-[(4-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1771, 1676 cm$^{-1}$; MS (ISP) 787.5 (M+H)$^+$ 11.13. (6R,7R)-7-[(Z)-2-(2-Amino-thiazol-4-yl)-2-cyclopentyloxyimino-acetylamino]-3-[(E)-1-[1-[2-(2,3-dihydro-indol-1-yl)-2-oxo-ethyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1770, 1669 cm$^{-1}$; MS (ISP) 783.5 (M+H)$^+$ 11.14. (6R,7R)-7-[(Z)-2-(2-Amino-thiazol-4-yl)-2-cyclopentyloxyimino-acetylamino]-3-[(E)-1-(1-methyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate IR (KBr) 1768, 1668 cm$^{-1}$; MS (ISP) 638.4 (M+H)$^+$ 11.15. (6R,7R)-7-[(Z)-2-(2-Amino-thiazol-4-yl)-2-cyclopentyloxyimino-acetylamino]-3-[(E)-1-[1-(2-hydroxy-ethyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1670 cm$^{-1}$; MS (ISP) 690.4 (M+Na)$^+$ 11.16. (6R,7R)-7-[(Z)-2-[2-(2-Amino-thiazol-4-yl)-2-cyclopentyloxyimnino]-acetylamino]-3-[(E)-1-(1-carbamoylmethyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate IR (KBr) 1766, 1665 cm$^{-1}$; MS (ISP) 681.4 (M+H)$^+$ 11.17. (6R,7R)-7-[(Z)-2-(2-Amino-thiazol-4-yl)-2-cyclopentyloxyimino-acetylamino]-3-[(E)-1-(1-benzyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate trifluoroacetic acid salt IR 1777, 1676 cm$^{-1}$; MS (ISP) 714.4 (M+H)$^+$ 11.18. (6R,7R)-7-[(Z)-2-(2-Amino-thiazol-4-yl)-2-cyclopentyloxyimino-acetylamino]-3-[(E)-1-[1-(4-cyano-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1670 cm$^{-1}$; MS (ISP) 739.3 (M+H)$^+$ 11.19. (6R,7R)-7-[(Z)-2-(2-Amino-thiazol-4-yl)-2-cyclopentyloxyimino-acetylamino]-3-[(E)-1-[1-(3-hydroxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate IR (KBr) 1769, 1664 cm$^{-1}$; MS (ISP) 730.4 (M+H)$^+$ 11.20. (6R,7R)-7-[(Z)-2-(2-Amino-thiazol-4-yl)-2-cyclopentyloxyimino-acetylamino]-3-[(E)-1-[1-(4-carboxyl-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate sodium salt IR (KBr) 1765, 1668 cm$^{-1}$; MS (ISP) 758.4 (M+H)$^+$ 11.21. (6R,7R)-7-[(Z)-2-(2-Amino-thiazol-4-yl)-2-cyclopentyloxyimino-acetylamino]-3-[(E )-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia1-aza-bicyclo[4.2.0]oct-2-ene-2-carboxylate IR (KBr) 1769, 1674 cm$^{-1}$; MS (ISP) 791.5 (M+H)$^+$ 11.22. (6R,7R)-7-[(Z)-2-(2-Amino-thiazol-4-yl)-2-cyclopentyloxyimino-acetylamino]-3-[(E)-1-[1-[(4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate IR (KBr) 1767, 1672 cm$^{-1}$; MS (ISP) 773.3 (M+H)$^+$ 11.23. (6R,7R)-7-[(Z)-2-(2-Amino-thiazol-4-yl)-2-cyclopentyloxyimino-acetylamino]-3-[(E)-1-[1-[(3-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate IR (KBr) 1770, 1665 cm$^{-1}$; MS (ISP) 773.3 (M+H)$^+$ 11.24. (6R,7R)-7-[(Z)-2-(2-Amino-thiazol-4-yl)-2-cyclopentyloxyimino-acetylamino]-3-[(E)-1-[1-[(5-methyl-[1,3,4]thiadiazol-2-ylcarbamoyl)-methyl]-pyridin-1-ium-3-ylmethyl]-2-oxo-pyrrolidin-3-ylidenemethyl]-8-oxo-6-thia-1-aza-bicyclo[4.2.0]oct-2-ene-2-carboxylate IR (KBr) 1769, 1671 cm$^{-1}$; MS (ISP) 779.2 (M+H)$^+$ 11.25. (6R,7R)-7-[(Z)-2-(2-Amino-thiazol-4-yl)-2-cyclopentyloxyimino-acetylamino]-3-[(E)-1-(1-methyl-pyridin-1-ium-2-ylmethyl)-2-oxo-pyrrolidin-3-ylidenemethyl]-8-oxo-5-thia-1-aza-bicyclo[4.2.0]oct-2-ene-2-carboxylate IR (KBr) 1775, 1675 cm$^{-1}$; MS (ISP) 638.3 (M+H)$^+$

EXAMPLE 12 preparation (8) ⟶ (10), scheme 1

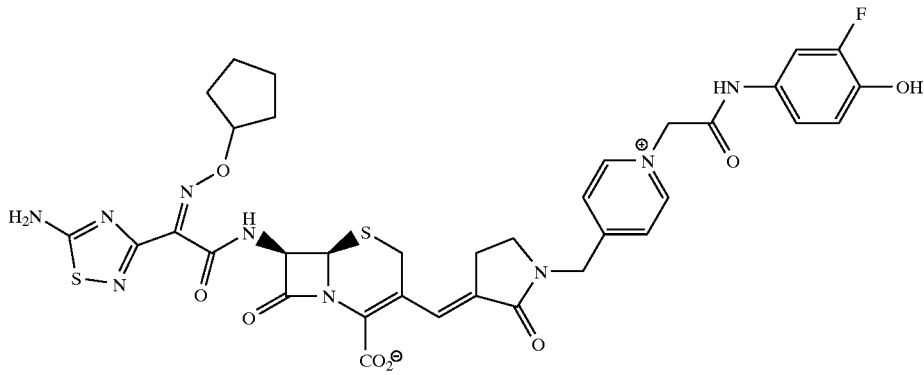

(6R,7R)-7-[(Z)-2-(5-Amino-[1,2,4]thiadiazol-3-yl)-2-cyclopentyloxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate A solution of (Z)-(5-amino-[1,2,4]thiadiazol-3-yl)-cyclopentyloxyimino-acetate 1-allyl-1-methyl-pyrrolidinium salt in 10 ml DMF was treated with HBTU (170 mg, 0.45 mmol) for 1.5 h at room temperature. (E)-(6R,7R)-7-Amino-3-[1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate trifluoroacetic acid salt (300 mg, 0.45 mmol) was added and the mixture was stirred for 78 h before it was concentrated in vacuo. The residue was dissolved in ethylacetate and extracted with water. The organic phase was evaporated and the residue triturated with diethylether. The product was purified by gel chromatography (MCI-gel, using a gradient of water with increasing concentrations of acetonitrile). Yield: 40 mg (11%).

IR(KBr) 1767, 1670 cm$^{-1}$; MS(ISP) 792.4 (M+H)$^{+.}$

EXAMPLE 13 preparation (6) ⟶ (11), scheme 2

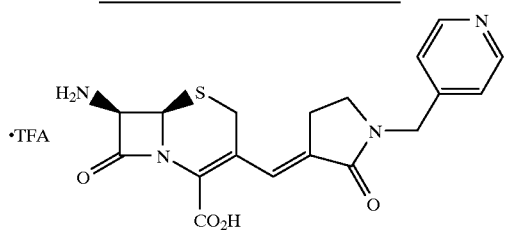

The following compounds were synthesized using the procedure described in example 7.

13.1.(E )-(6R,7R)-7-Amino-8-oxo-3-(2-oxo-1-pyridin-4-ylmethyl-pyrrolidin-3-ylidenemethyl)-5-thia-1-aza-bicyclo[4.2.0]oct-2-ene-2-carboxylic acid trifluoroacetic acid salt IR (KBr) 1782, 1679 cm$^{-1}$; MS (ISP) 387.2 (M+H)$^+$ 13.2. (E )-(6R,7R)-7-Amino-8-oxo-3-(2-oxo-1-pyridin-3-ylmethyl-pyrrolidin-3-ylidenemethyl)-5-thia-1-aza-bicyclo[4.2.0]oct-2-ene-2-carboxylic acid trifluoroacetic acid salt IR (KBr) 1782, 1677 cm$^{-1}$; MS (ISP) 387.2 (M+H)$^+$ 13.3. (E )-(6R,7R)-7-Amino-8-oxo-3-(2-oxo-1-pyridin-2-ylmethyl-pyrrolidin-3-ylidenemethyl)-5-thia-1-aza-bicyclo[4.2.0]oct-2-ene-2-carboxylic acid trifluoroacetic acid salt IR (KBr) 1787, 1682 cm$^{-1}$; MS (ISP) 387.2 (M+H)$^+$

EXAMPLE 14 preparation (11)→(12), scheme 2

The following compounds were synthesized using the procedure described in example 8. They were converted into their sodium salts by adjusting the aqueous suspension of the acid with 1N sodium hydroxide solution to pH 6. Purification was accomplished by reversed phase chromatography (MERCK Lichroprep RP-18 silica gel, 25–40μ, using a gradient of water with increasing concentrations of acetonitrile).

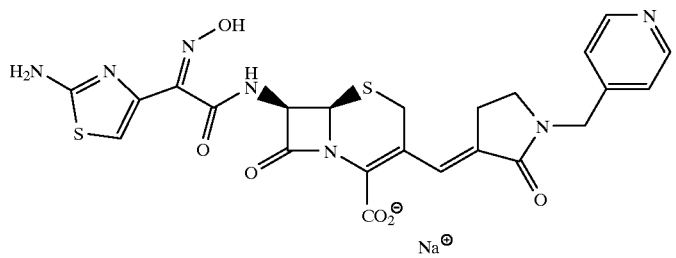

14.1. (6R,7R)-7-[(Z)-2-(2-Amino-thiazol-4-yl)-2-hydroxyimino-acetylamino]-8-oxo-3-[(E)-2-oxo-1-pyridin-4-ylmethyl-pyrrolidin-3-ylidenemethyl]-5-thia- 1-aza-bicyclo[4.2.0]oct-2-ene-2-carboxylic acid sodium salt IR (KBr) 1765, 1666 cm$^{-1}$; MS (ISP) 600.3 (M+2Na−H)$^+$ 14.2. (6R,7R)-7-[(Z)-2-(2-Amino-thiazol-4-yl)-2-hydroxyimino-acetylamino]-8-oxo-3-[(E)-2-oxo-1-pyridin-3-ylmethyl-pyrrolidin-3-ylidenemethyl]-5-thia- 1-aza-bicyclo[4.2.0]oct-2-ene-2-carboxylic acid IR (KBr) 1769, 1666 cm$^{-1}$; MS (ISN) 554.1 (M−H)$^-$ 14.3. (6R,7R)-7-[(Z)-2-(2-Amino-thiazol-4-yl)-2-hydroxyimino-acetylamino]-8-oxo-3-[(E)-2-oxo- 1-pyridin-2-ylmethyl-pyrrolidin-3-ylidenemethyl]-5-thia-1-aza-bicyclo[4.2.0]oct-2-ene-2-carboxylic acid IR (KBr) 1775, 1668 cm$^{-1}$; MS (ISP) 556.2 (M+H)$^+$

EXAMPLE 15

The following compounds were synthesized using the procedure described in example 11. They were converted into their sodium salts by adjusting the aqueous suspension of the acid with 1N sodium hydroxide solution to pH 6. Purification was accomplished by reversed phase chromatography (MERCK Lichroprep RP-18 silica gel, 25–40µ, using a gradient of water with increasing concentrations of acetonitrile).

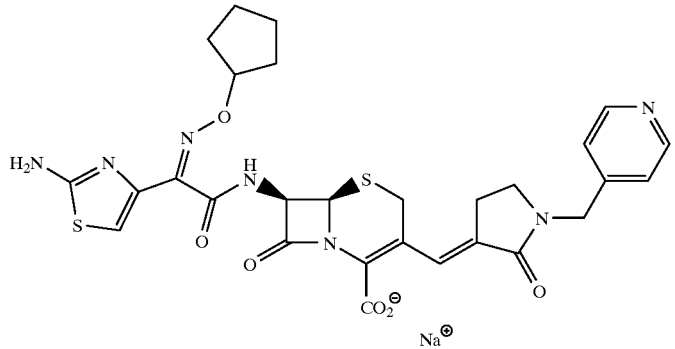

15.1. (6R,7R)-7-[(Z)-(2-Amino-thiazol-4-yl)-2-cyclopentyloxyimino-acetyl-amino]-8-oxo-3-[(E)-2-oxo-1-pyridin-4-ylmethyl-pyrrolidin-3-ylidenemethyl]-5-thia-1-aza-bicyclo[4.2.0]oct-2-ene-2-carboxylic acid sodium salt IR (KBr) 1763 cm$^{-1}$; MS (ISP) 624.3 (M−Na+2H)$^+$ 15.2. ($^6$R,$^7$R)-7-[(Z)-2-(2-Amino-thiazol-4-yl)-2-cyclopentyloxyimino-acetyl-amino]-8-oxo-3-[(E)-(2-oxo-1-pyridin-3-ylmethyl-pyrrolidin-3-ylidenemethyl)-5-thia-1-aza-bicyclo[4.2.0]oct-2-ene-2-carboxylic acid sodium salt IR (KBr) 1770, 1671 cm$^{-1}$; MS (ISP) 624.2 (M+H)$^+$ 15.3. (6R,7R)-7-[(Z)-2-(2-Amino-thiazol-4-yl)-2-cyclopentyloxyimino-acetyl-amino]-8-oxo-3-[(E)-2-oxo-1-pyridin-2-ylmethyl-pyrrolidin-3-ylidenemethyl]-5-thia-1-aza-bicyclo[4.2.0]oct-2-ene-2-carboxylic acid IR (KBr) 1776, 1669 cm$^{-1}$; MS (ISP) 624.2 (M+H)$^+$

EXAMPLE 16

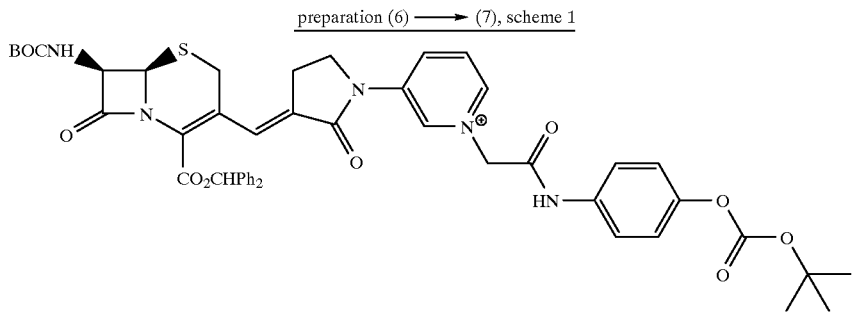

preparation (6) ⟶ (7), scheme 1

16.1. (E)-(6R,7R)-3-[3-(2-Benzhydryloxycarbonyl-7-tert-butoxycarbonylamino-8-oxo-5-thia-1-aza-bicyclo[4.2.0]oct-2-en-3-ylmethylene)-2-oxo-pyrrolidin-1-yl]-1-[(4-tert-butoxycarbonyloxy-phenylcarbamoyl)-methyl]-pyridinium bromide A solution of (E)-(6R,7R)-7-tert-butoxycarbonylamino-8-oxo-3-(2-oxo-1-pyridin-3-yl-pyrrolidin-3-ylidenemethyl)-5-thia-1-aza-bicyclo[4.2.0]oct-2-ene-2-carboxylic acid benzhydryl ester (as described and prepared in EP 620225-A1) (639 mg, 1.0 mmol) in 10 ml dichloromethane/acetonitrile (1:1) was treated with carbonic acid 4-(2-bromo-acetylamino)-phenyl ester tert-butyl ester (494 mg, 1.5 mmol) for 48 h. The solvent was removed in vacuo and the residue triturated with diethylether. Yield: 857 mg (88%)

IR(KBr) 1786, 1758 cm$^{-1}$; MS(ISP) 888.4 (M)$^+$.

According to the procedure set forth in the preceding example, the following additional compounds were prepared:

16.2. (E )-(6R,7R)-3-[3-(2-Benzhydryloxycarbonyl-7-tert-butoxycarbonylamino-8-oxo-5-thia-1-aza-bicyclo[4.2.0]oct-2-en-3-ylmethylene)-2-oxo-pyrrolidin-1-yl]-1-carbamoylmethyl-pyridinium bromide IR (KBr) 1783, 1703 cm$^{-1}$; MS (ISP) 696.4 (M)$^+$ 16.3. (E)-(6R,7R)-3-[3-(2-Benzhydryloxycarbonyl-7-tert-butoxycarbonylamino-8-oxo-5-thia-1-aza-bicyclo[4.2.0]oct-2-en-3-ylmethylene)-2-oxo-pyrrolidin-1-yl]-1-methyl-pyridinium iodide IR(KBr) 1782, 1712 cm$^{-1}$; MS (ISP) 653.5 (M)$^+$.

EXAMPLE 17

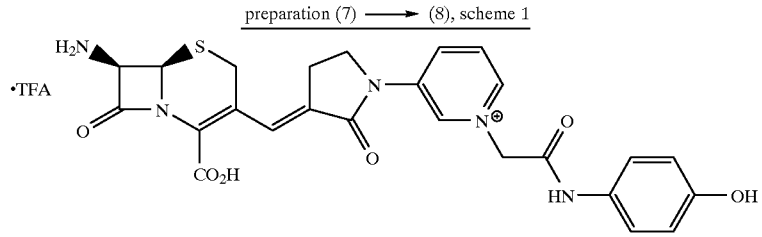

preparation (7) ⟶ (8), scheme 1

17.1. (E)-6r,7R)-7-Amino-3-[1-[1-[(4-hydroxy-phenylcarbamoyl)-methyl]-pyridin-1-ium-3-yl]-2-oxo-pyrrolidin-3-ylidenemethyl]-8-oxo-5-thia-1-aza-bicyclo[4.2.0]oct-2-ene-2-carboxylate trifluoroacetic acid salt A solution of (E)-(6R,7R)-3-[3-(2-benzhydryloxycarbonyl-7-tert-butoxy-carbonylamino-8-oxo-5-thia-1-aza-bicyclo[4.2.0]oct-2-en-3-ylmethylene)-2-oxo-pyrrolidin-1-yl]-1-carbamoylmethyl-pyridinium bromide (840 mg, 0.867 mmol) in 10 ml dichloromethane and 0.84 ml anisol was treated at 0–5° C. with 4.2 ml trifluoroacetic acid. After stirring for 2 h at room temperature, the mixture was concentrated in vacuo and the residue poured on 200 ml cold diethylether. The precipitate was collected by filtration yielding 518 mg (94%) of the product as a beige powder.

IR(KBr) 1776, 1683 cm$^{-1}$; MS(ISP) 522.3 (M+H)$^+$.

According to the procedure set forth in the preceding example, the following additional compounds were prepared:

17.2. (E)-(6R,7R)-7-Amino-3-[1-(1-carbamoylmethyl-pyridin-1-ium-3-yl)-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1780, 1692 cm$^{-1}$; MS (ISP) 430.3 (M+H)$^+$ 17.3. (E)-(6R,7R)-7-Amino-3-[1-(1-methyl-pyridin-1-ium-3-yl)-2-oxo-pyrrolidin-3-ylidenemethyl]-8-oxo-5-thia-1-aza-bicyclo[4.2.0]oct-2-ene-2-carboxylate IR (KBr) 1756, 1617 cm$^{-1}$; MS (ISP) 387.4 (M+H)$^+$

EXAMPLE 18 preparation (8)→(10) scheme 1

The following compounds were synthesized using the procedure described in example 8.

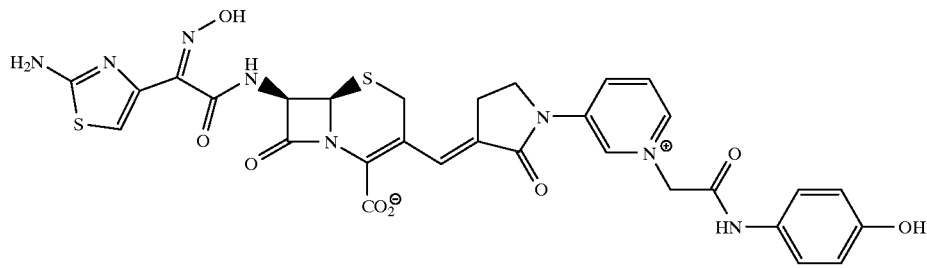

18.1. (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-3-yl]-2-oxo-pyrrolidin-3-ylidenemethyl]-8-oxo-5-thia-1-aza-bicyclo[4.2.0]oct-2-ene-2-carboxylate IR (KBr) 1769, 1678 cm$^{-1}$; MS (ISP) 691.2 (M+H)$^+$ 18.2. (6R,7R)-7-[(Z)-2-(2-Amino-thiazol-4-yl)-2-hydroxyimino-acetylamino]-3-[(E)-1-(1-carbamoylmethyl-pyridin-1-ium-3-yl)-2-oxo-pyrrolidin-3-ylidenemethyl]-8-oxo-5-thia-1-aza-bicyclo[4.2.0]oct-2-ene-2-carboxylate trifluoroacetic acid salt IR (KBr) 1769, 1692 cm$^{-1}$; MS (ISP) 599.3 (M+H)$^+$ 18.3. (6R,7R)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-5-thia-1-aza-bicyclo[4.2.0]oct-2-ene-2-carboxylate IR (KBr) 1767, 1618 cm$^{-1}$; MS (ISP) 556.0 (M+H)$^+$

EXAMPLE 19 preparation (8)→(10) scheme 1

The following compounds were synthesized using the procedure described in example 11.

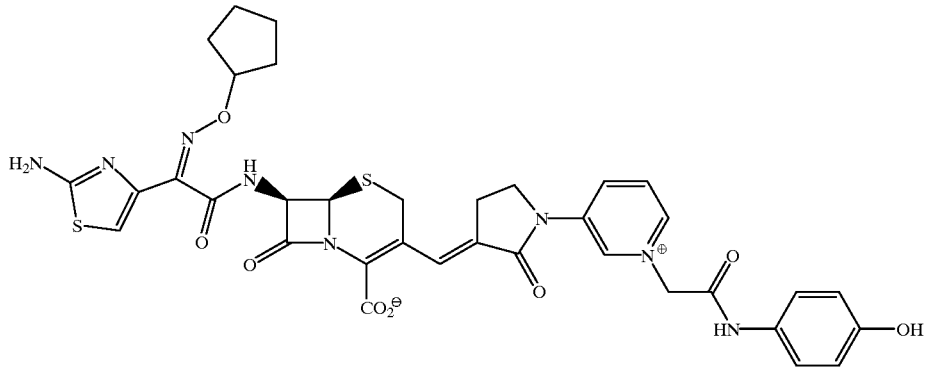

19.1. (6R,7R)-7-[(Z)-2-(2-Arnino-thiazol-4-yl)-2-cyclopentyloxyiniino-acetyl-amino]-3-[(E)-1-[1-[(4-hydroxy-phenylcarbamoyl)-methyl]-pyridin-1-ium-3-yl]-2-oxo-pyrrolidin-3-ylidenemethyl]-8-oxo-5-thia-1-aza-bicyclo[4.2.0]oct-2-ene-2-carboxylate IR (KBr) 1770, 1676 cm$^{-1}$; MS (ISP) 759.5 (M+H)$^+$ 19.2. (6R,7R)-7-[(Z)-2-(2-Amino-thiazol-4-yl)-2-cyclopentyloxyimino-acetyl-amino]-3-[(E)-1-(1-carbamoylmethyl-pyridin-1-ium-3-yl)-2-oxo-pyrrolidin-3-ylidenemethyl]-8-oxo-5-thia-1-aza-bicyclo[4.2.0]oct-2-ene-2-carboxylate IR (KBr) 1773, 1688 cm$^{-1}$; MS (ISP) 667.4 (M+H)$^+$ 19.3. (6R,7R)-7-[(Z)-2-(2-Amino-thiazol-4-yl)-2-cyclopentyloxyimino-acetylamino]-3-[(E )-1-(1-methyl-pyridin-1-ium-3-yl)-2-oxo-pyrrolidin-3-ylidenemethyl]-8-oxo-5-thia-1-aza-bicyclo[4.2.0]oct-2-ene-2-carboxylate IR (KBr) 1775, 1679 cm$^{-1}$; MS (ISP) 624.2 (M+H)$^+$

EXAMPLE 20

20.1. (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]pyridin-1-ium-4-ylmethyl]-2-oxo-pyrrolidin-3-ylidenemethyl]-8-oxo-5-thia-1-aza-bicyclo[4.2.0]-oct-2-ene-2-carboxylate dihydrochloride To a suspension of (6R,7R)-7-[(Z)-2-(2-amino-thiazol-4-yl)-2-hydroxyimino-acetylamino]-3-[(E )-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate (578.2 mg, 0.8 mmol) in 32 ml methanol was added 1 ml of a saturated solution of HCl in diethylether. The resulting solution was added with stirring into 500 ml diethylether. The solid material was collected by filtration, washed with diethylether and dried.

Yield: 564 mg beige powder

Microanalysis: calculated for $C_{31}H_{27}FN_8O_8S_2$. 2 HCl

| | | | | | |
|---|---|---|---|---|---|
| calc. | C 46.80 | H 3.67 | N 14.08 | S 8.06 | Cl 8.91 |
| found | C 46.93 | H 3.36 | N 14.17 | S 8.18 | Cl 9.02 |

According to the procedure set forth in the preceding example, the following additional compounds were prepared:

20.2. (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia- 1-aza-bicyclo[4.2.0]-oct-2-ene-2-carboxylate methanesulfonate Microanalysis: calculated for $C_{31}H_{27}FN_8O_8S_2 \cdot 2\ CH_3SO_3H$

| | | | | |
|---|---|---|---|---|
| calc. | C 43.52 | H 3.94 | N 12.14 | S 13.89 |
| found | C 43.61 | H 3.66 | N 11.93 | S 13.95 |

20.3. (6,R7R)-7-[(Z)-2-(2-Amino-thiazol-4-yl)-2-hydroxyimino-acetylnino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8oxo-thia-1-aza-bicyclo[4.2.0]-oct2-ene-2 carboxylate hydrogensulfate Microanalysis: calculated for $C_{31}H_{27}FN_8O_8S_2 \cdot 2\ H_2SO4$

| | | | | |
|---|---|---|---|---|
| calc. | C 40.52 | H 3.40 | N 12.20 | S 13.96 |
| found | C 42.02 | H 3.42 | N 11.99 | S 13.96 |

We claim:
1. A compound of formula I

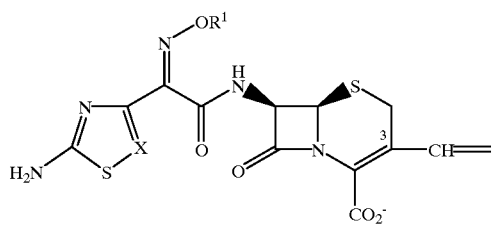

wherein
$R^1$ is hydrogen, lower alkyl, cycloalkyl or acetyl;
X is CH or N;
n is 0, 1 or 2;
m is 0 or 1;
$R^2$ is lower alkyl, ω-hydroxy alkyl, benzyl or lower alkyl-heterocyclyl, where the heterocyclyl group is a 4-, 5- or 6-membered saturated or unsaturated N-heterocycle, the benzyl and the heterocyclyl group being unsubstituted or substituted with at least one of the groups amino, cyano, carboxy, halogen, hydroxy, lower alkyl, lower alkoxy or $-CONR_2$, where R is hydrogen or lower alkyl; or $R^2$ is $-CH_2CONR^4R^5$;
wherein $R^4$, $R^5$ are each independently hydrogen, c)-hydroxyalkyl, phenyl, benzyl, naphthyl or 4-, 5- or 6-membered saturated or unsaturated N-heterocycle, the phenyl, benzyl, naphthyl or heterocyclyl groups being unsubstituted or substituted with at least one of the groups optionally protected hydroxy, halogen, optionally substituted lower alkyl, optionally substituted lower alkoxy, ω-hydroxyalkyl or cyano;

or the groups $R^4$ and $R^5$ form together a group of formula

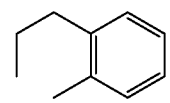

with the proviso that when pyridinium ring A is pyridinium-4-yl, m is 1; as well as esters thereof which are readily hydrolyzable in vivo, pharmaceutically acceptable salts of said compounds and hydrates of the compounds of formula I and of their esters and salts.

2. The compound according to claim 1, wherein n is 1.

3. The compound according to claim 2, having the formula

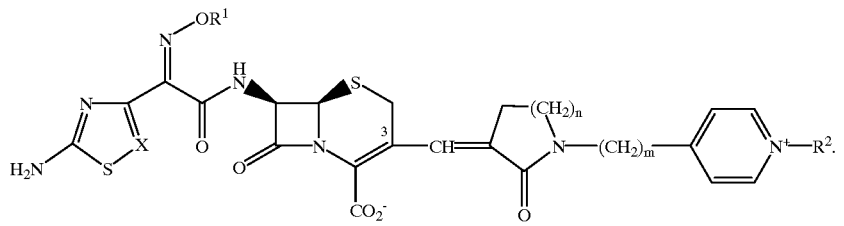

-continued

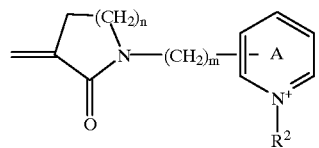

4. A method for treating bacterial infection in a mammal comprising administering to said mammal a compound of formula

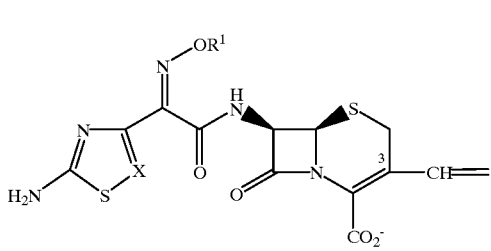

-continued

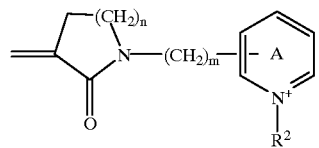

wherein

R¹ is hydrogen, lower alkyl, cycloalkyl or acetyl;

X is CH or N;

n is 0, 1 or 2;

m is 0 or 1;

R² is lower alkyl, ω-hydroxy alkyl, benzyl or lower alkyl-heterocyclyl, where the heterocyclyl group is a 4-, 5- or 6-membered saturated or unsaturated N-heterocycle, the benzyl and the heterocyclyl group being unsubstituted or substituted with at least one of the groups amino, cyano, carboxy, halogen, hydroxy, lower alkyl, lower alkoxy or —CONR₂, where R is hydrogen or lower alkyl; or R² is —CH₂CONR⁴R⁵; wherein R⁴, R⁵ are each independently hydrogen, ω-hydroxyalkyl, phenyl, benzyl, naphthyl or heterocyclyl, the phenyl, benzyl, naphthyl or 4-, 5- or 6-membered saturated or unsaturated N-heterocycle groups being unsubstituted or substituted with at least one of the groups optionally protected hydroxy, halogen, optionally substituted lower alkyl, optionally substituted lower alkoxy, ω-hydroxyalkyl or cyano;

or the groups R⁴ and R⁵ form together a group of formula

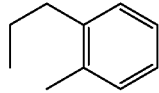

with the proviso that when pyridinium ring A is pyridinium-4-yl, m is 1; as well as esters thereof which are readily hydrolyzable in vivo, pharmaceutically acceptable salts of said compounds and hydrates of the compounds of formula I and of their esters and salts; and a therapeutically inert carrier.

5. The compound according to claim 3, wherein R¹ is hydrogen.

6. The compound according to claim 5, wherein X is CH.

7. The compound according to claim 6, wherein R² is lower alkyl, benzyl which is unsubstituted or substituted with at least one of the groups cyano, carboxy, or hydroxy, or —CH₂CONR⁴R⁵.

8. The compound according to claim 7, wherein R² is lower alkyl.

9. The compound according to claim 8, (6R,7R)-7-[(Z)-2-(2-Amino-thiazol-4-yl)-2-hydroxyimino-acetylamino]-3-[(E)- 1-(1-methyl-pyridin-1-ium-4-ylmethyl)-2-oxo-pyrrolidin-3-ylidenemethyl]-8-oxo-5-thia-1 -aza-bicyclo [4.2.0]oct-2-ene-2-carboxylate.

10. The compound according to claim 7, wherein R² is benzyl which is unsubstituted or substituted with at least one of the groups cyano, carboxy, or hydroxy.

11. The compound according to claim 10, (6R,7R)-7-[(Z)-2-(2-Amino-thiazol-4-yl)-2-hydroxyimino-acetylamino]-3-[(E)-1-(1-benzyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate.

12. The compound according to claim 10, (6R,7R)-7-[(Z)-2-(2-Amino-thiazol-4-yl)-2-hydroxyimino-acetylamino]-3-[(E)-1-[1-(4-cyano-benzyl)-pyridin 1-ium-4-ylmethyl]-2-oxo-pyrrolidin-3-ylidenemethyl]-8-oxo-5-thia-1-aza-bicyclo[4.2.0]oct-2-ene-2-carboxylate.

13. The compound according to claim 10, (6R,7R)-7-[(Z)-2-(2-Amino-thiazol-4-yl)-2-hydroxyimino-acetylamino]-3-[(E)-1-[1-(3-hydroxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

14. The compound according to claim 10, (6R,7R)-7-[(Z)-2-(2-Amino-thiazol-4-yl)-2-hydroxyimino-acetylamino]-3-[(E)-1-[1-(4-carboxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate sodium salt.

15. The compound according to claim 7, wherein R² is —CH2CONR⁴R⁵.

16. The compound according to claim 15, wherein R⁴ is hydrogen and R⁵ is hydrogen, ω-hydroxy alkyl, phenyl which is unsubstituted or substituted with at least one of the groups hydroxy, halogen, lower alkyl which is unsubstituted or substituted with at least one halogen, or lower alkoxy, benzyl which is unsubstituted or substituted with at least one of the groups cyano, carboxy, or hydroxy, heterocycle which is unsubstituted or substituted with lower alkyl, or the groups R⁴ and R⁵ form together a group of formula

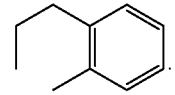

17. The compound according to claim 16, wherein R⁵ is hydrogen, namely the compound (6R,7R)-7-[(Z)-2-(2-Amino-thiazol-4-yl)-2-hydroxyimino-acetylamino]-3-[(E)-1-(1-carbamoylmethyl-pyridin-1-ium-4-ylmethyl)-2-oxo-pyrrolidin-3-ylidenemethyl]-8-oxo-5-thia-1-aza-bicyclo [4.2.0]oct-2-ene-2-carboxylate.

18. The compound according to claim 16, wherein R⁵ is ω-hydroxy alkyl.

19. The compound according to claim 18, (6R,7R)-7-[(Z)-2-(2-Amino-thiazol-4-yl)-2-hydroxyimino-acetylamino]-3-[(E)-1-[1-[(2-hydroxy-ethylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

20. The compound according to claim 16, wherein R⁵ is phenyl which is unsubstituted or substituted with at least one of the groups hydroxy, halogen, lower alkyl which is unsubstituted or substituted with at least one halogen or lower alkoxy.

21. The compound according to claim 20, (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

22. The compound according to claim 20, (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

23. The compound according to claim 20, (6R,7R)-7-[(Z)-2-(2-Amino-thiazol-4-yl)-2-hydroxyimino-acetylamino]-3-[(E)-1-[1-[(3-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

24. The compound according to claim 20, (6R,7R)-7-[(Z)-2-(2-Amino-thiazol-4-yl)-2-hydroxyimino-acetylamino]-3-[(E)-1-[1-[(2-hydroxy-phenylcarbamoyl)-methyl]-pyridin-1-ium-4-ylmethyl]-2-oxo-pyrrolidin-3-ylidenemethyl)-8-oxo-5-thia-1-aza-bicyclo[4.2.0]oct-2-ene-2-carboxylate.

25. The compound according to claim 20, (6R,7R)-7-[(Z)-2-(2-Amino-thiazol-4-yl)-2-hydroxyimino-acetylamino]-3-[(E)-1-[1-[(2-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

26. The compound according to claim 20, (6R,7R)-7-[(Z)-2-(2-Amino-thiazol-4-yl)-2-hydroxyimino-acetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo-[4.2.0]oct-2-ene-2-carboxylate.

27. The compound according to claim 20, (6R,7R)-7-[(Z)-2-(2-Amino-thiazol-4-yl)-2-hydroxyimino-acetylamino]-3-[(E)-1-[1-[(4-hydroxy-3-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo-[4.2.0]oct-2-ene-2-carboxylate.

28. The compound according to claim 20, (6R,7R)-7-[(Z)-2-(2-Amino-thiazol-4-yl)-2-hydroxyimino-acetylamino]-3-[(E)-1-[1-[(3,4-difluoro-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

29. The compound according to claim 20, (6R,7R)-7-[(Z)-2-(2-Amino-thiazol-4-yl)-2-hydroxyimino-acetylamino]-3-[(E)-1-[1-[(4-methoxy-phenylcarbamoyl)-methyl]-pyridin-1-ium-4-ylmethyl]-2-oxo-pyrrolidin-3-ylidenemethyl ]-8-oxo-5-thia-1-aza-bicyclo[4.2.0]oct-2-ene-2-carboxylate.

30. The compound according to claim 20, (6R,7R)-7-[(Z)-2-(2-Amino-thiazol-4-yl)-2-hydroxyimino-acetylamino]-3-[(E)-1-[1-[(4-hydroxy-2-trifluoromethyl-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

31. The compound according to claim 16, wherein $R^5$ is benzyl which is substituted with hydroxy, namely the compound (6R,7R)-7-[(Z)-2-(2-Amino-thiazol-4-yl)-2-hydroxyimino-acetylamino]-3-[(E)-1-[1-[(3-hydroxy-benzylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

32. The compound according to claim 16, wherein $R^5$ is heterocycle which is substituted with lower alkyl.

33. The compound according to claim 32, (6R,7R)-7-[(Z)-2-(2-Amino-thiazol-4-yl)-2-hydroxyimino-acetylamino]-3-[(E)-1-[1-(5-methyl-[1,3,]thiadiazol-2-ylcarbamoyl)-methyl]-pyridin-1-ium-4-ylmethyl]-2-oxo-pyrrolidin-3-ylidenemethyl]-8-oxo-5-thia-1-aza-bicyclo-[4.2.0]oct-2-ene-2-carboxylate.

34. The compound according to claim 32, (6R,7R)-7-[(Z)-2-(2-Amino-thiazol-4-yl)-2-hydroxyimino-acetylamino]-3-[(E)-1-[1-[(2-methyl-benzooxazol-5-ylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

35. The compound according to claim 16, wherein $R^4$ and $R^5$ form together a group of formula

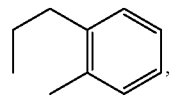

namely the compound (6R,7R)-7-[(Z)-2-(2-Amino-thiazol-4-yl)-2-hydroxyimino-acetylamino]-3-[(E)-1-[1-[2-(2,3-dihydro-indol-1-yl)-2-oxo-ethyl]-pyridin1-ium-4-ylmethyl]-2-oxo-pyrrolidin-3-ylidenemethyl]-8-oxo-5-thia-1-aza-bicyclo[4.2.0]oct-2-ene-2-carboxylate.

36. The compound according to claim 5, wherein X is N.

37. The compound according to claim 36, wherein $R^2$ is —$CH_2CONR^4R^5$.

38. The compound according to claim 37, wherein $R^4$ is hydrogen and $R^5$ is phenyl which is unsubstituted or substituted with at least one of the groups hydroxy, halogen, or lower alkoxy.

39. The compound according to claim 38, (6R,7R)-7-[(Z)-2-(5-Amino-[1,2,4]thiadiazol-3-yl)-2-hydroxyimino-acetylamino]-3-[(E)-1-[1-[(3-filuoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

40. The compound according to claim 38, (6R,7R)-7-[(Z)-2-(5-Amino-[1,2,4]thiadiazol-3-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo-[4.2.0]oct-2-ene-2-carboxylate.

41. The compound according to claim 4, wherein $R^1$ is acetoxy.

42. The compound according to claim 41, wherein X is CH.

43. The compound according to claim 42, wherein $R^2$ is ω-hydroxy alkyl.

44. The compound according to claim 43, (6R,7R)-7-[(Z)-2-Acetoxyimino-2-(2-amino-thiazol-4-yl)-acetylamino]-3-[(E)-1-[1-(2-hydroxy-ethyl)-pyridin-1-ium-1-ylmethyl]-2-oxo-pyrrolidin-3-ylidenemethyl]-8-oxo-5-thia-1-aza-bicyclo[4.2.0]oct-2-ene-2-carboxylate.

45. The compound according to claim 4, wherein $R^1$ is cycloalkyl.

46. The compound according to claim 45, wherein $R^1$ is cyclopentyl.

47. The compound according to claim 46, wherein X is CH.

48. The compound according to claim 47, wherein $R^2$ is lower alkyl, benzyl which is unsubstituted or substituted with at least one of the groups cyano, carboxy, or hydroxy, ω-hydroxy alkyl, or —$CH_2CONR^4R^5$.

49. The compound according to claim 48, wherein $R^2$ is lower alkyl.

50. The compound according to claim 49, (6R,7R)-7-[(Z)-2-(2-Amino-thiazol-4-yl)-2-cyclopentyloxyimino-acetylamino]-3-[(E)-1-(1-methyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate.

51. The compound according to claim 48, wherein $R^2$ is benzyl which is unsubstituted or substituted with at least one of the groups cyano, carboxy, or hydroxy.

52. The compound according to claim 51, (6R,7R)-7-[(Z)-2-(2-Amino-thiazol-4-yl)-2-cyclopentyloxyimino-acetylamino]-3-[(E)-1-(1-benzyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate trifluoroacetic acid salt.

53. The compound according to claim 51, (6R,7R)-7-[(Z)-2-(2-Amino-thiazol-4-yl)-2-cyclopentyloxyimino-acetylamino]-3-[(E)-1-[1-(4-cyano-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

54. The compound according to claim 51, (6R,7R)-7-[(Z)-2-(2-Amino-thiazol-4-yl)-2-cyclopentyloxyimino-acetylamino]-3-[(E)-1-[1-(3-hydroxy-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

55. The compound according to claim 51, (6R,7R)-7-[(Z)-2-(2-Amino-thiazol-4-yl)-2-cyclopentyloxyimino-acetylamino]-3-[(E)-1-[1-(4-carboxyl-benzyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate sodium salt.

56. The compound according to claim 48, wherein $R^2$ is —$CH_2CONR^4R^5$.

57. The compound according to claim 56, wherein $R^4$ is hydrogen and $R^5$ is hydrogen, ω-hydroxy alkyl, phenyl which is unsubstituted or substituted with at least one of the groups hydroxy, halogen, or lower alkoxy, benzyl which is unsubstituted or substituted with at least one of the groups cyano, carboxy, or hydroxy, hetereocycle which is unsubstituted or substituted with lower alkyl, or the groups $R^4$ and $R^5$ form together a group of formula

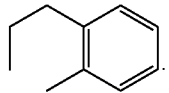

58. The compound according to claim 57, wherein $R^5$ is hydrogen, namely the compound (6R,7 R)-7-[(Z)-2- [2-(2-Amino-thiazol-4-yl)-2-cyclopentyloxyimino]-acetylamino]-3-[(E)-1-(1-carbamoylmethyl-pyridin-1-ium-4-ylmethyl)-2-oxo-pyrrolidin-3-ylidenemethyl]-8-oxo-5-thia-1-aza-bicyclo[4.2.0]oct-2-ene-2-carboxylate.

59. The compound according to claim 57, wherein $R^5$ is ω-hydroxy alkyl.

60. The compound according to claim 59, (6R,7R)-7-[(Z)-2-(2-Amino-thiazol-4-yl)-2-cyclopentyloxyimino-acetylamino]-3-[(E)-1-[1-[(2-hydroxy-ethylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

61. The compound according to claim 57, wherein $R^5$ is phenyl which is unsubstituted or substituted with at least one of the groups hydroxy, halogen, or lower alkoxy.

62. The compound according to claim 61, (6R,7R)-7-[(Z)-2-(2-Amino-thiazol-4-yl)-2-cyclopentyloxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

63. The compound according to claim 61, (6R,7R)-7-[(Z)-2-(2-Amino-thiazol-4-yl)-2-cyclopentyloxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

64. The compound according to claim 61, (6R,7R)-7-(Z)-2-(2-Amino-thiazol-4-yl)-2-cyclopentyloxyimino-acetylamino]-3-[(E)-1-[1-[(3-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

65. The compound according to claim 61, (6R,7R)-7-[(Z)-2-(2-Amino-thiazol-4-yl)-2-cyclopentyloxyimino-acetylamino]-3-[(E)-1-[1-[(2-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

66. The compound according to claim 61, (6R,7R)-7-[(Z)-2-(2-Amino-thiazol-4-yl)-2-cyclopentyloxyimino-acetylamino]-3-[(E)-1-[1-[(2-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

67. The compound according to claim 61, (6R,7R)-7-[(Z)-2-(2-Amino-thiazol-4-yl)-2-cyclopentyloxyimino-acetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

68. The compound according to claim 61, (6R,7R)-7-[(Z)-2-(2-Amino-thiazol-4-yl)-2-cyclopentyloxyimino-acetylamino]-3-[(E)-1-[1-[(4-hydroxy-3-methoxy-phenylcarbamoyl)-methyl]-pyridin-1-um-4-ylmethyl]-2-oxo-pyrrolidin-3-ylidenemethyl]-8-oxo-5-thia-1-aza-bicyclo[4.2.0]oct-2-ene-2-carboxylate.

69. The compound according to claim 61, (6R,7R)-7-[(Z)-2-(2-Amino-thiazol-4-yl)-2-cyclopentyloxyimino-acetylamino]-3-[(E)-1-[1-[(3,4-difluoro-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

70. The compound according to claim 61, (6R,7R)-7-[(Z)-2-(2-Amino-thiazol-4-yl)-2-cyclopentyloxyimino-acetylamino]-3-[(E)-1-[1-[(4-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

71. The compound according to claim 57, wherein $R^5$ is benzyl which is substituted with hydroxy, namely the compound (6R,7R)-7-[(Z)-2-(2-Amino-thiazol-4-yl)-2-cyclopentyloxyimino-acetylamino]-3-[(E)-1-[1-[(3-hydroxy-benzylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

72. The compound according to claim 57, wherein $R^5$ is heterocycle which is substituted with lower alkyl.

73. The compound according to claim 72, (6R,7R)-7-[(Z)-2-(2-Amino-thiazol-4-yl)-2-cyclopentyloxyimino-acetylamino]-3-[(E)-1-[1-[(5-methyl-[1,3,4]thiadiazol-2-ylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

74. The compound according to claim 57 wherein $R^4$ and $R^5$ form together a group of formula

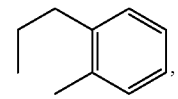

namely the compound (6R,7R)-7-[(Z)-2-(2-Amino-thiazol-4-yl)-2-cyclopentyloxyimino-acetylamino]-3-[(E)-1-[1-[2-(2,3-dihydro-indol-1-yl)-2-oxo-ethyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

75. The compound according to claim 48, wherein $R^2$ is ω-hydroxy alkyl.

76. The compound according to claim 75, (6R,7R)-7-[(Z)-2-(2-Amino-thiazol-4-yl)-2-cyclopentyloxyiminoacetylamino]-3-[(E)-1-[1-(2-hydroxy-ethyl)-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

77. The compound according to claim 46, wherein X is N.

78. The compound according to claim 77, wherein $R^2$ is —$CH_2CONR^4R^5$.

79. The compound according to claim 78, wherein $R^4$ is hydrogen and $R^5$ is phenyl which is unsubstituted or substituted with at least one of the groups hydroxy, halogen, or lower alkoxy.

80. The compound according to claim 79, (6R,7R)-7-[(Z)-2-(5-Amino-[1,2,4]thiadiazol-3-yl)-2-cyclopentyloxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

81. The compound according to claim 2, having the formula

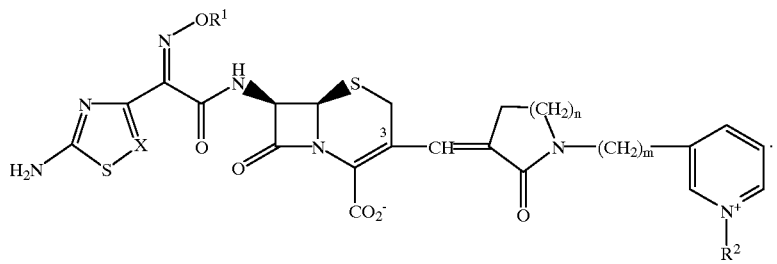

82. The compound according to claim 81, wherein m is 1.

83. The compound according to claim 82, wherein $R^1$ is hydrogen.

84. The compound according to claim 83, wherein X is CH.

85. The compound according to claim 84, wherein $R^2$ is —$CH_2CONR^4R^5$.

86. The compound according to claim 85, wherein $R^4$ is hydrogen and $R^5$ is phenyl which is unsubstituted or substituted with at least one of the groups hydroxy, halogen, or lower alkoxy, or heterocycle which is unsubstituted or substituted with lower alkyl.

87. The compound according to claim 86, wherein $R^5$ is phenyl which is unsubstituted or substituted with at least one of the groups hydroxy, halogen, or lower alkoxy.

88. The compound according to claim 87, (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

89. The compound according to claim 87, (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

90. The compound according to claim 87, (6R,7R)-7-[(Z)-2-(2-Amino-thiazol-4-yl)-2-hydroxyimino-acetylamino]-3-[(E)-1-[1-[(3-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

91. The compound according to claim 86, wherein $R^5$ is heterocycle which is unsubstituted or substituted with lower alkyl.

92. The compound according to claim 91, (6R,7R)-7-[(Z)-2-(2-Amino-thiazol-4-yl)-2-hydroxyimino-acetylamino]-3-[(E)-1-[1-[(5-methyl-[1,3,4]thiadiazol-2-ylcarbamoyl)-methyl]-pyridin-1-ium-3-ylmethyl-2-oxo-pyrrolidin-3-ylidenemethyl]-8-oxo-5-thia-1-aza-bicyclo[4.2.0]oct-2-ene-2-carboxylate.

93. The compound according to claim 81, wherein m is 0.

94. The compound according to claim 93, wherein $R^1$ is hydrogen.

95. The compound according to claim 94, wherein X is CH.

96. The compound according to claim 95, wherein $R^2$ is lower alkyl or —$CH_2CONR^4R^5$.

97. The compound according to claim 96, wherein $R^2$ is lower alkyl.

98. The compound according to claim 97, (6R,7R)-7-[(Z)-2-(2-Amino-thiazol-4-yl)-2-hydroxyimino-acetylamino]-3-[(E)-1-(1-methyl-pyridin-1-ium-3-yl)-2-oxo-pyrrolidin-3-ylidenemethyl]-8-oxo-5-thia-1-aza-bicyclo[4.2.0]oct-2-ene-2-carboxylate.

99. The compound according to claim 96, wherein $R^2$ is —$CH_2CONR^4R^5$.

100. The compound according to claim 99, wherein $R^4$ is hydrogen and $R^5$ is hydrogen or phenyl which is unsubstituted or substituted with at least one of the groups hydroxy, halogen, or lower alkoxy.

101. The compound according to claim 100, wherein $R^5$ is hydrogen, namely the compound (6R,7R)-7-[(Z)-2-(2-Amino-thiazol-4-yl)-2-hydroxyimino-acetylamino]-3-[(E)-1-(1-carbamoylmethyl-pyridin-1-ium-3-yl)-2-oxo-pyrrolidin-3-ylidenemethyl]-8-oxo-5-thia-1-aza-bicyclo[4.2.0]oct-2-ene-2-carboxylate trifluoroacetic acid salt.

102. The compound according to claim 100, wherein $R^5$ is phenyl which is substituted with at least one of the groups hydroxy, halogen, or lower alkoxy.

103. The compound according to claim 102, (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-3-yl]-2-oxo-pyrrolidin-3-ylidenemethyl]-8-oxo-5-thia-1-aza-bicyclo[4.2.0]oct-2-ene-2-carboxylate.

104. The method according to claim 4, wherein X is N.

105. The compound according to claim 81, wherein $R^1$ is cycloalkyl.

106. The compound according to claim 105, wherein $R^1$ is cyclopentyl.

107. The compound according to claim 106, wherein $R^2$ is —$CH_2CONR^4R^5$.

108. The compound according to claim 107, wherein $R^4$ is hydrogen and $R^5$ is phenyl which is unsubstituted or substituted with at least one of the groups hydroxy, halogen, or lower alkoxy, or heterocycle which is unsubstituted with lower alkyl.

109. The compound according to claim 108, wherein $R^5$ is phenyl which is unsubstituted or substituted with at least one of the groups hydroxy, halogen, or lower alkoxy.

110. The compound according to claim 109, (6R,7R)-7-[(Z)-2-(2-Amino-thiazol-4-yl)-2-cyclopentyloxyimino-acetylamino]-3-[(E)-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

111. The compound according to claim 109, (6R,7R)-7-[(Z)-2-(2-Amino-thiazol-4-yl)-2-cyclopentyloxyimino-acetylamino]-3-[(E)-1-[1-[(4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

112. The compound according to claim 109, (6R,7R)-7-[(Z)-2-(2-Amino-thiazol-4-yl)-2-cyclopentyloxyimino-acetylamino]-3-[(E)-1-[1-[(3-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

113. The compound according to claim 108, wherein $R^5$ is heterocycle which is substituted with lower alkyl.

114. The compound according to claim 113, (6R,7R)-7-[(Z)-2-(2-Amino-thiazol-4-yl)-2-cyclopentyloxyimino-acetylamino]-3-[(E)-1-[1-[(5-methyl-[1,3,4]thiadiazol-2-ylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

115. The method according to claim 104, wherein $R^2$ is —$CH_2CONR^4R^5$.

116. The compound according to claim 81, wherein $R^1$ is cycloalkyl.

117. The compound according to claim 116, wherein $R^1$ is cyclopentyl.

118. The compound according to claim 117, wherein $R^2$ is lower alkyl or —$CH_2CONR^4R^5$.

119. The compound according to claim 118, wherein $R^2$ is lower alkyl.

120. The compound according to claim 119, (6R,7R)-7-[(Z)-2-(2-Amino-thiazol-4-yl)-2-cyclopentyloxyimino-acetylamino]-3-[(E)-1-(1-methyl-pyridin-1-ium-3-yl)-2-oxo-pyrrolidin-3-ylidenemethyl]-8-oxo-5-thia-1-aza-bicyclo[4.2.0]oct-2-ene-2-carboxylate.

121. The compound according to claim 118, wherein $R^2$ is —$CH_2CONR^4R^5$.

122. The compound according to claim 121, wherein $R^4$ is hydrogen and $R^5$ is hydrogen or phenyl which is unsubstituted or substituted with at least one of the groups hydroxy, halogen, or lower alkoxy.

123. The compound according to claim 122, wherein $R^5$ is phenyl which is unsubstituted or substituted with at least one of the groups hydroxy, halogen, or lower alkoxy.

124. The compound according to claim 123, (6R,7R)-7-[(Z)-2-(2-Amino-thiazol-4-yl)-2-cyclopentyloxyimino-acetylarnino]-3-[(E)-1-[1-[(4-hydroxy-phenylcarbamoyl)-methyl]-pyridin-1-ium-3-yl]-2-oxo-pyrrolidin-3-ylidenemethyl]-8-oxo-5-thia-1-aza-bicyclo[4.2.0]oct-2-ene-2-carboxylate.

125. The compound according to claim 122, wherein Rs is hydrogen, namely, (6R,7R)-7-[(Z)-2-(2-Amino-thiazol-4-yl)-2-cyclopentyloxyimino-acetylamino]-3-[(E)-1-(1-carbamoylmethyl-pyridin-1-ium-3-yl)-2-oxo-pyrrolidin-3-ylidenemethyl]-8-oxo-5-thia-1-aza-bicyclo[4.2.0]oct-2-ene-2-carboxylate.

126. The compound according to claim 2, having the formula

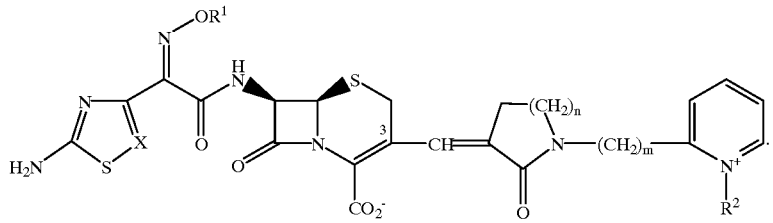

127. The compound according to claim 126, wherein m is 1.

128. The compound according to claim 127, wherein $R^1$ is hydrogen.

129. The compound according to claim 128, wherein X is CH.

130. The compound according to claim 129, wherein $R^2$ is lower alkyl or benzyl which is unsubstituted or substituted with at least one of the groups cyano, carboxy, or hydroxy.

131. The compound according to claim 130, wherein $R^2$ is lower alkyl.

132. The compound according to claim 131, (6R,7R)-7-[(Z)-2-(2-Amino-thiazol-4-yl)-2-hydroxyimino-acetylarnino]-3-[(E)-1-(1-methyl-pyridin-1-ium-2-ylmethyl)-2-oxo-pyrrolidin-3-ylidenemethyl]-8-oxo-5-thia-1-aza-bicyclo[4.2.0]oct-2-ene-2-carboxylate.

133. The compound according to claim 130, wherein $R^2$ is benzyl which is unsubstituted or substituted with at least one of the groups cyano, carboxy, or hydroxy.

134. The compound according to claim 133, wherein $R^2$ is benzyl which is substituted with hydroxy, namely the compound (6R,7R)-7-[(Z)-2-(2-Amino-thiazol-4-yl)-2-hydroxyimino-acetylarnino]-3-[(E)-1-[1-(3-hydroxy-benzyl)-pyridin-1-ium-2-ylmethyl]-2-oxo-pyrrolidin-3-ylidenemethyl]-8-oxo-5-thia-1-aza-bicyclo[4.2.0]oct-2-ene-2-carboxylate.

135. The compound according to claim 127, wherein $R^1$ is cycloalkyl.

136. The compound according to claim 135, wherein $R^1$ is cyclopentyl.

137. The compound according to claim 136, wherein X is CH.

138. The compound according to claim 137, wherein $R^2$ is lower alkyl.

139. The compound according to claim 138, (6R,7R)-7-[(Z)-2-(2-Amino-thiazol-4-yl)-2-cyclopentyloxyimino-acetylamino]-3-[(E)-1-(1-methyl-pyridin-1-ium-2-ylmethyl)-2-oxo-pyrrolidin-3-ylidenemethyl]-8-oxo-5-thia-1-aza-bicyclo[4.2.0]oct-2-ene-2-carboxylate.

140. A pharmaceutical composition comprising a therapeutically effective amount of a compound of formula I

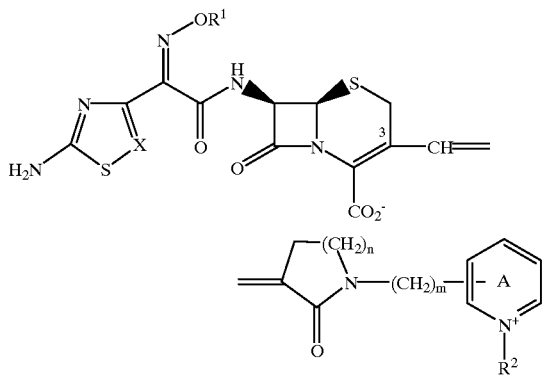

wherein

R¹ is hydrogen, lower alkyl, cycloalkyl or acetyl;

X is CH or N;

n is 0, 1 or 2;

m is 0 or 1;

R² is lower alkyl, ω-hydroxy alkyl, benzyl or lower alkyl-heterocyclyl, where the heterocyclyl group is a 4-, 5- or 6-membered saturated or unsaturated N-heterocycle the benzyl and the heterocyclyl group being unsubstituted or substituted with at least one of the groups amino, cyano, carboxy, halogen, hydroxy, lower alkyl, lower alkoxy or —CONR₂, where R is hydrogen or lower alkyl; or R² is —CH₂CONR⁴R⁵; wherein R⁴, R⁵ are each independently hydrogen, ω-hydroxyalkyl, phenyl, benzyl, naphthyl or 4-, 5- or 6-membered saturated or unsaturated N-heterocycle, the phenyl, benzyl, naphthyl or heterocyclyl groups being unsubstituted or substituted with at least one of the groups optionally protected hydroxy, halogen, optionally substituted lower alkyl, optionally substituted lower alkoxy, ω-hydroxyalkyl or cyano;

or the groups R⁴ and R⁵ form together a group of formula

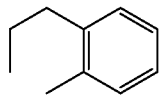

with the proviso that when pyridinium ring A is pyridinium-4-yl, m is 1; as well as esters thereof which are readily hydrolyzable in vivo, pharmaceutically acceptable salts of said compounds and hydrates of the compounds of formula I and of their esters and salts; and a therapeutically inert carrier.

141. The composition according to claim 140, wherein X is CH.

142. The composition according to claim 141, wherein R² is —CH₂CONR⁴R⁵.

143. The composition according to claim 142, wherein R⁴ is hydrogen and R⁵ is phenyl which is unsubstituted or substituted with at least one of the groups hydroxy, halogen, lower alkyl which is unsubstituted or substituted with at least one halogen, or lower alkoxy.

144. The composition according to claim 143, (6R,7R)-7-[(Z)-2-(2-Amino-thiazol-4-yl)-2-hydroxyimino-acetylamino]-3-[(E)-1-[1 -[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

145. The composition according to claim 143, (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

146. The composition according to claim 143, (6R,7R)-7-[(Z)-2-(2-Amino-thiazol-4-yl)-2-hydroxyimino-acetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

147. The composition according to claim 143, (6R,7R)-7-[(Z)-2-(2-Amino-thiazol-4-yl)-2-hydroxyimino-acetylamino]-3-[(E)-1-[1-[(4-hydroxy-3-methoxy-phenylcarbamoyl)-methyl]-pyridin-1ium-4-ylmethyl]-2-oxo-pyrrolidin-3-ylidenemethyl]-8-oxo-5-thia-1-aza-bicyclo[4.2.0]oct-2-ene-2-carboxylate.

148. The composition according to claim 143, (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

149. The composition according to claim 140, wherein X is N.

150. The composition according to claim 149, wherein R² is —CH₂CONR⁴R⁵.

151. The composition according to claim 150, wherein R⁵ is phenyl which is unsubstituted or substituted with at least one of the groups hydroxy, halogen, lower alkyl which is unsubstituted or substituted with at least one halogen, or lower alkoxy.

152. The composition according to claim 151, (6R,7R)-7-[(Z)-2-(5-Amino-[1,2,4]thiadiazol-3-yl)-2-hydroxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

153. The composition according to claim 151, (6R,7R)-7-[(Z)-2-(5-Amino-[1,2,4]thiadiazol-3-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

154. The method according to claim 115, wherein R⁴ is hydrogen and R⁵ is phenyl which is unsubstituted or substituted with at least one of the groups hydroxy, halogen, lower alkyl which is unsubstituted or substituted with at least one halogen, or lower alkoxy.

155. The method according to claim 154, wherein X is CH.

156. The method according to claim 155, wherein R² is —CH₂CONR⁴R⁵.

157. The method according to claim 156, wherein R⁴ is hydrogen and R⁵ is phenyl which is unsubstituted or substituted with at least one of the groups hydroxy, halogen, lower alkyl which is unsubstituted or substituted with at least one halogen, or lower alkoxy.

158. The method according to claim 157, (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

159. The method according to claim 157, (6R,7R)-7-[(Z)-2-(2-Amino-thiazol-4-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

160. The method according to claim 157, (6R,7R)-7-[(Z)-2-(2-Amino-thiazol-4-yl)-2-hydroxyimino-acetylamino]-3-[(E)-1-[1-[(3-chloro-4-hydroxy-phenylcarbamoyl)-methyl]-pyridin-1-ium-4-ylmethyl]-2-oxo-pyrrolidin-3-ylidenernethyl]-8-oxo-5-thia-1-aza-bicyclo[4.2.0]oct-2-ene-2-carboxylate.

161. The method according to claim 157, (6R,7R)-7-[(Z)-2-(2-Amino-thiazol-4-yl)-2-hydroxyimino-acetylamino]-3-[(E)-1-[1-[(4-hydroxy-3-methoxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

162. The method according to claim 157, (6R,7R)-7-[(Z)-2-(2-Amino-thiazol-4-yl)-2-hydroxyimino-acetylamino]-3-[(E)-1-[1-[(3-fluoro-4-hydroxy-phenylcarbamoyl)-methyl]-pyridin-1-ium-3-ylmethyl]-2-oxo-pyrrolidin-3-ylidenemethyl]-8-oxo-5-thia-1-aza-bicyclo[4.2.0]oct-2-ene-2-carboxylate.

163. The method according to claim 154, (6R,7R)-7-[(Z)-2-(5-Amino-[1,2,4]thiadiazol-3-yl)-2-hydroxyimino-acetylamino]-3-[(E)-1-[1-[(3-fluoro-4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

164. The method according to claim 154, (6R,7R)-7-[(Z)-2-(5-Amino-[1,2,4]thiadiazol-3-yl)-2-hydroxyimino-acetylamino]-3-[(E)-1-[1-[(4-hydroxy-phenylcarbamoyl)-methyl]-pyridin-1-ium-4-ylmethyl]-2-oxo-pyrrolidin-3-ylidenemethyl]-8-oxo-5-thia-1-aza-bicyclo[4.2.0]oct-2-ene-2-carboxylate.

* * * * *